(12) United States Patent
Maksym et al.

(10) Patent No.: US 9,109,240 B2
(45) Date of Patent: Aug. 18, 2015

(54) **SERINOL PRODUCTION IN GLYCEROL CATABOLISM DEFICIENT *ESCHERICHIA COLI* STRAINS**

(71) Applicants: BASF SE, Ludwigshafen (DE); Westfaelische Wilhelms-Universitaet Muenster, Muenster (DE)

(72) Inventors: Lukas Maksym, Cologne (DE); Alexander Steinbuechel, Altenberge (DE); Bjoern Andreessen, Muenster (DE)

(73) Assignees: BASF SE, Ludwigshafen (DE); Westfaelische Wilhelms Universitaet Muenster, Muenster (DE)

( * ) Notice: Subject to any disclaimer, the term of this patent is extended or adjusted under 35 U.S.C. 154(b) by 0 days.

(21) Appl. No.: 14/018,725

(22) Filed: Sep. 5, 2013

(65) Prior Publication Data
US 2014/0080187 A1    Mar. 20, 2014

Related U.S. Application Data

(60) Provisional application No. 61/700,956, filed on Sep. 14, 2012.

(51) Int. Cl.
*C12P 13/00* (2006.01)
*C12N 9/10* (2006.01)
*C12N 9/90* (2006.01)

(52) U.S. Cl.
CPC .............. *C12P 13/001* (2013.01); *C12N 9/1096* (2013.01); *C12N 9/90* (2013.01)

(58) Field of Classification Search
None
See application file for complete search history.

(56) References Cited

PUBLICATIONS

Andreesen et al, "Biotechnological conversion of glycerol to 2-amino-1,3-propanediol (serinol) in recombinant *Escherichia coli*.", Appl Microbiol Biotechnol (2012) 93:357-365. DOI 10.1007/s00253-011-3364-6.*
Tolia et al., "Strategies for protein coexpression in *Escherichia coli*", Nature Methods, Jan. 2006, 3(1):55-64.*

* cited by examiner

*Primary Examiner* — Suzanne M Noakes
(74) *Attorney, Agent, or Firm* — Marshall, Gerstein & Borun LLP

(57) ABSTRACT

The invention is about *E. coli* host cells which are capable to convert glycerol to serinol. Furthermore, a process for producing serinol is disclosed, which comprises culturing *E. coli* host cells inactive for triosephosphate isomerase and active for dihydroxyacetone phosphate aminotransferase to convert glycerol to serinol, induction of conversion from glycerol to serinol by adding at least glycerol to the cell culture, and isolating serinol from the cell culture.

13 Claims, No Drawings

SERINOL PRODUCTION IN GLYCEROL CATABOLISM DEFICIENT ESCHERICHIA COLI STRAINS

CROSS-REFERENCE TO RELATED APPLICATIONS

This application claims the benefit of U.S. provisional patent application No. 61/700,956, filed Sep. 14, 2012, incorporated herein by reference in its entirety.

This application claims priority of application with number U.S. 61/700,956, which is incorporated by reference in its entirety.

The present invention relates to the production of serinol in *Escherichia coli* strains. More specifically, the *E. coli* strains are deficient in glycerol catabolism for this purpose.

Serinol (2-amino-1,3-propanediol; FIG. 1) belongs to the group of aminoalcohols and is a structural analog of the amino acid serine.

FIG. 1: Structural formula of serinol

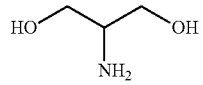

Amino alcohols like serinol are widely used as precursors for non-ionic X-ray contrast agents like 1-N,3-N-bis(1,3-dihydroxypropan-2-yl)-5-[(2S)-2-hydroxypropanamido]-2,4,6-triiodobenzene-1,3-dicarboxamide (iopamidol), which is, for example, distributed as iopamiro (Bracco Diagnostics Inc.). Serinol constitutes also an intermediate for drugs dealing with pain treatment. Furthermore, chiral (1R,2R) phenylserinols have been used as precursors in chloramphenicol synthesis.

Notably, serinol is used as an intermediate in rhizobitoxine [2-amino-4-(2-amino-3-hydropropoxy)-trans-but-3-enoic acid] synthesis of the plant pathogen *Burkholderia andropogonis*, the legume symbiont *Bradyrhizobium japonicum* and its close relative *Bradyrhizobium elkanii*. Transposon insertion (Tn5) in the rtxA gene of *B. elkanii* caused a rhizobitoxine null mutant. The N-terminal domain of the amino acid sequence of rtxA contains a motif homologous to aminotransferases (Ruan et al. 1993, *Bradyrhizobium japonicum* rhizobiotoxine genes and putative enzyme functions: expression requires a translational frameshift, Proc. Natl. Acad. Sci. USA, 90:2641-2645) and has 24% identity and 40% similarity to the aminotransferase of *Methanobacterium thermoautotrophicum* (Smith et al. 1997, Complete genome sequence of *Methanobacterium thermoautotrophicum* deltaH: functional analysis and comparative genomics, J. Bacteriol., 179:7135-7155). Mutants with a disruption in the gene coding for the N-terminal region of the protein were defective in serinol accumulation (Yasuta et al. 2001, DNA sequence and mutational analysis of rhizobiotoxine biosynthesis genes in *Bradyrhizobium elkanii*, Appl. Environ. Microbiol., 67:4999-5009).

Based on the growing importance of serinol as an important intermediate for several chemical applications the interest arose to use renewable resources for its production.

Andreeβen and Steinbüchel (2012, Biotechnological conversion of glycerol to 2-amino-1,3-propanediol (serinol) in recombinant *Escherichia coli*, Appl. Microbiol. Biotechnol. 93:357-365) disclose the biotechnological conversion of glycerol to serinol. Either the bifunctional enzyme dihydroxyacetone phosphate aminotransferase/dihydrorhizobitoxine synthase of *Bradyrhizobium elkanii* USD94 or only the N-terminal domain comprising the first reaction respectively, was expressed in recombinant *E. coli* strain HMS174 (DE3) using different expression vectors with and without IPTG.

The highest serinol contents were achieved in the pCDF-Duet-1 vector (induced 0.95 g/l; uninduced 2.8 g/l). Induction with IPTG is assumed to lead to inclusion body formation and lower serinol production. Using a different *E. coli* host strain i.e. C43 with the same vector, i.e. pCDFDuet-1 also lead to a decreased serinol production (230 mg/l). Also, heat induction was disclosed achieving higher levels of serinol compared to IPTG induction.

However, with respect to the C43 mutant strain for rtxA, it was described that glutamic acid is the preferred cosubstrate for the transamination of dihydroxyacetone phosphate to serinolphosphate, which is the essential step in the serinol synthesis.

As the intercellular serinol contents achieved seemed to be toxic for the cells, it was considered to react serinol into the corresponding acylester, however the approach failed to work successfully. It was discussed that the deletion or decrease in triosephosphate isomerase (Noble et al. 1993, Structure of triosephosphate isomerase from *Escherichia coli* determined at 2.6 Å resolution, Acta Crystallogr. Sect. D: Biol., 49:403-417) activity could lead to a higher metabolic flux through the artificial serinol synthesis pathway.

The lasting interest in producing serinol by using renewable resources created the problem to be solved for this invention to tackle the issue of toxicity as major bottleneck in the biotechnological serinol production. Furthermore, it was wished to increase thereby the overall serinol production as another issue. Therefore, a process with increased production of serinol in an *E. coli* stain should be achieved, as well as the establishment of a more efficient *E. coli* strain for serinol production.

The problem was solved by establishing a process for producing serinol, which comprises i) culturing *E. coli* host cells inactive for triosephosphate isomerase and active for dihydroxyacetone phosphate aminotransferase to convert glycerol to serinol ii) induction of conversion from glycerol to serinol by adding at least glycerol to the cell culture iii) isolating serinol from the cell culture.

Other embodiments comprise the same process, wherein the *E. coli* host cells are in addition inactive for methylglyoxal synthase and/or wherein the *E. coli* host cells are inactive for a functional glp DNA-binding transcriptional repressor.

A further embodiment comprises such processes, wherein the expression of active dihydroxyacetone phosphate aminotransferase is achieved by introducing an expression vector into the host cells comprising the transgene coding for dihydroxyacetone phosphate aminotransferase which is active for conversion of glycerol to serinol.

The invention also comprises isolated recombinant expression vectors comprising the transgene encoding for dihydroxyacetone phosphate aminotransferase which is active for conversion of glycerol to serinol and wherein the expression of the dihydroxyacetone phosphate aminotransferase is inducible with IPTG.

Additionally, the invention comprises recombinant *E. coli* strains active for dihydroxyacetone phosphate aminotransferase to convert glycerol to serinol, wherein triosephosphate isomerase is inactivated in the *E. coli* host cells. Other embodiments comprise such a strain, wherein methylglyoxal synthase is inactivated and/or the glp DNA-binding transcriptional repressor is inactivated additionally.

Other embodiments are recombinant E. coli strains of the invention, wherein the expression of the dihydroxyacetone phosphate aminotransferase capable to convert glycerol to serinol is introduced into the said strain by using an expression vector as disclosed.

Further embodiments comprise recombinant E. coli strains of the invention comprising the transgene encoding for dihydroxyacetone phosphate aminotransferase which is active for conversion of glycerol to serinol, comprising further parts of the rtx operon additionally.

Part of the invention is also the use of any E. coli strain of the invention, to convert glycerol to serinol.

DETAILED DESCRIPTION

Regarding cells and their culture the following applies herein

The term "wild type" is meant to designate the microorganism which is used as source for genetic modification according to the invention. Preferred wild type cells of the invention are E. coli cells. More preferably, these E. coli cells, also called E. coli strain, have the genetic background of BL21(DE3), C43(DE3), HMS174(DE3), Rosetta-gami B(DE3)/pLysS, MG1655 (see Table 1). More preferred is the genetic background of HMS174(DE3) and MG1655.

The terms "control" or "reference" are exchangeable and are meant to serve as microorganism for comparative purposes. Therefore, the control or reference cells have to be treated identically or as identical as possible, saying that only conditions or properties might be different which do not influence the quality of the tested property. The recombinant control or reference cells should be of the same genetic background as the recombinant cells which should be compared in terms of the "change of a property". Sometimes, the control or reference cells are identical with the wild type cells. Preferred herein are recombinant E. coli cells which are modified in terms to express active dihydroxyacetone phosphate aminotransferase capable to convert glycerol into serinol. More preferably, these E. coli cells, also called E. coli strain, have the genetic background of BL21(DE3), C43(DE3), HMS174 (DE3), Rosetta-gami B(DE3)/pLysS, MG1655 (see Table 1). More preferred is the genetic background of HMS174(DE3) and MG1655.

Despite the wild type cells which are the source of mutation, "host cells" are those cells which are mutated. However, the host cells are compared to control or reference cells for the purpose of identifying the "change of a property". Preferred host cells herein are mutated E. coli cells. More preferably, these mutated E. coli strains are of the genetic background of BL21(DE3), C43(DE3), HMS174(DE3), Rosetta-gami B(DE3)/pLysS, MG1655 (see Table 1). More preferred are the genetic backgrounds of HMS174(DE3) and MG1655.

Cells are normally grown in growth or cell culture medium. The one skilled in the art is aware of the specifics to be acknowledged in the selection of the optimal growth medium of specific cells. The culture of engineered host cells might necessitate addition of special additives to a growth medium to optimize the desired change of a property.

The "change of a property" is to be understood as the activity, expression level or amount of a gene product or the metabolite or product content changed in a specific volume relative to a corresponding volume of a control or reference, including the de novo creation of the activity or expression. Herein, the change of several properties is described, e.g. the desired expression of a special polypeptide allowing the conversion of glycerol into serinol. Other properties to be changed herein, is e.g. the inactivation of the enzyme activity or the inactivation of the repressor function of polypeptides involved in the pathway of said conversion.

The "change of this property" is meant to be understood to be either established or "increased" (or "raised", "extended", "enhanced", "improved"; this terms indicating a gain are interchangeable) relating to the comparison of a mutated microorganism with its control microorganism. The measures to indicate absolute amounts of product produced are e.g. g/l. The measures indicating a relative change in productivity of a microorganism compared to its control microorganism is provided in % w/w.

"Capable of producing" means that a microorganism of the invention in fact produces or provides a specific product, in the present case serinol, if not otherwise stated. Herein, cells "capable of producing" a product are host cells which are able to produce serinol by conversion from glycerol. "Capable to convert glycerol to serinol" herein is meant to be understood that microorganisms with this capability are active for dihydroxyacetone phosphate aminotransferase.

Regarding the product to be produced the following applies herein

The term "conversion", as used herein, means the process of generating a product from an educt or substrate by the action of microorganisms. More specifically, the educt is glycerol and the product is serinol within the context of the invention. The "bio(technological)"-conversion has to be distinguished from a chemical reaction which also is often called conversion. The one skilled in the art is normally able to identify the distinction within the context. The amount of product produced can be quantitatively stated in absolute measures like g/l or in relative numbers like a "rate of conversion" (or reaction) in % w/w. In general, totality of conversion is desired, meaning e.g. that 100% w/w of glycerol

TABLE 1

E. coli strains

| Strain | Description | Reference or source |
|---|---|---|
| BL21(DE3) | F− ompT gal dcm ion hsd$S_B$($r_B^-$ $m_B^-$) λ(DE3 [lacI lacUV5-T7 gene 1 ind1 sam7 nin5]) | Novagen |
| C43(DE3) | F− ompT gal dcm ion hsd$S_B$($r_B^-$ $m_B^-$) λ(DE3 [lacI lacUV5-T7 gene 1 ind1 sam7 nin5]) | Lucigen |
| HMS174(DE3) | F− recA1 hsdR($r_{K12}^-$ $m_{K12}^+$) (Rif$^r$) λ(DE3) | Novagen |
| Rosetta-gami B(DE3)/pLysS | Δ(ara-leu)7697 ΔlacX74 ΔphoA PvuII phoR araD139 ahpC gale galK rpsL (DE3) F'[lac$^+$ lacI$^q$ pro] gor522::Tn10 trxB pLysSRARE (Cam$^R$, Str$^R$, Tet$^R$) | Novagen |
| MG1655 | F− λ− ilvG− rfb-50 rph-1 | Blattner et al. (1997) | should be converted into serinol. The "bio(technological)" conversion of glycerol into serinol is reported to follow the pathway shown in FIG. 2.

FIG. 2: the conversion of glycerol to serinol as disclosed by Andreeβen and Steinbüchel (2012, Appl. Microbiol. Biotechnol. 93:357-365)

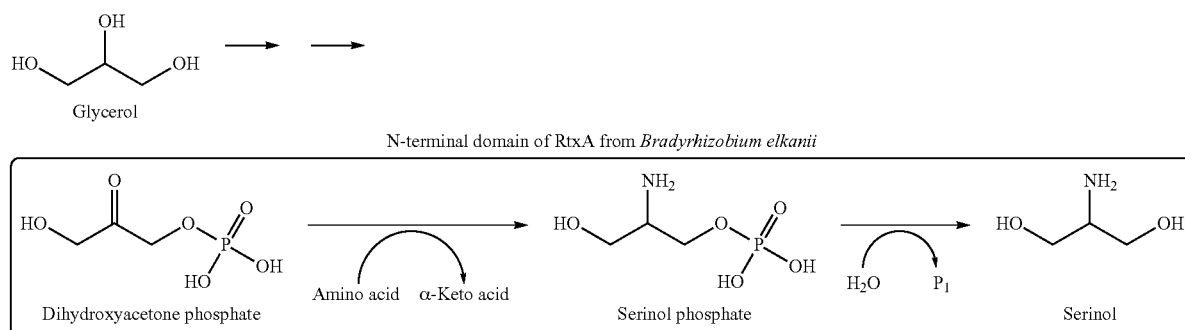

The "rate of conversion" (or reaction) specifies the effectively obtained product in relation to its educt in % w/w from the specific conversion or reaction. Losses of educt might result from the exploitation of the educt not only for the conversion to the desired product, meaning that the product might e.g. serve for other purposes like being a carbon source for cell growth. Preferably, the rate of conversion (or conversion rate) is at least 10%, 20%, 30%, 40%, 50%, 60%, 70%, 80%, 90%, or 100%. More preferably it is at least 20% up to 100%. Most preferably the conversion rate is at least 30% up to 100%. The rate of conversion indicates the productivity of the microorganism of the invention compared to its control microorganism, which is a measure of efficiency of production (total output per one unit of a total input).

Regarding the molecular biology aspects of the invention the following applies:

Genetic modification are the result of "mutations" which are in general accidental changes in the genomic sequence of a DNA (i.e. polynucleotide), e.g. caused by radiation, viruses, transposons and mutagenic chemicals (induced mutations), as well as errors that occur during meiosis or DNA replication (spontaneous mutations). Such mutations may change the expression of those genes in a (micro)organism which are affected, resulting in a changed profile of functional proteins (or polypeptides) which then cause a change of properties (or property) in the respective (micro)organism.

"Site-directed mutagenesis" is a molecular biology technique. The goal is to create a mutation a defined site in a DNA molecule (or polynucleotide). The basic procedure requires the synthesis of a short DNA primer. This synthetic primer contains the desired mutation and is complementary to the template DNA around the mutation site so it can hybridize with the DNA in the gene of interest. The mutation may be a single base change (a point mutation), multiple base changes, deletion or insertion. The single-stranded primer is then extended using a DNA polymerase, which copies the rest of the gene. The gene thus copied contains the mutated site, and is then introduced into a host cell as a vector and cloned. Finally, mutants are selected. A large number of site-directed mutagenesis methods are available to the one skilled in the art (Sambrook et al. 1989, Molecular cloning: a laboratory manual, 2$^{nd}$ edit, Cold Spring Harbor Laboratory, Cold Spring Harbor, N.Y.).

A deletion (also called gene deletion, deficiency, or deletion mutation) (sign: Δ) is a mutation (a genetic aberration) in which a part of a chromosome or a sequence of DNA is missing. Deletion is the loss of genetic material. Any number of nucleotides can be deleted, from a single base to an entire piece of chromosome.

An insertion (also called an insertion mutation) is the addition of one or more nucleotide base pairs into a DNA sequence. Insertions can be anywhere in size from one base pair incorrectly inserted into a DNA sequence to a section of one chromosome inserted into another.

A frame-shift mutation is a mutation caused by insertion or deletion of a number of nucleotides that is not evenly divisible by three from a DNA sequence. Due to the triplet nature of gene expression by codons, the insertion or deletion can disrupt the reading frame, or the grouping of the codons, resulting in a completely different translation from the original. The earlier in the sequence the deletion or insertion occurs, the more altered the protein produced is. In contrast, any insertion or deletion that is evenly divisible by three is termed an in-frame mutation.

A nonsense mutation is a point mutation in a sequence of DNA that results in a premature stop codon, or a nonsense codon in the transcribed mRNA, and possibly a truncated, and often nonfunctional protein product.

Missense mutations or non-synonymous mutations are types of point mutations where a single nucleotide is changed to cause substitution of a different amino acid. This in turn can render the resulting protein nonfunctional.

A neutral mutation is a mutation that occurs in an amino acid codon which results in the use of a different, but chemically similar, amino acid. The similarity between the two is enough that little or no change is often rendered in the protein. For example, a change from AAA to AGA will encode arginine, a chemically similar molecule to the intended lysine.

Silent mutations are mutations that do not result in a change to the amino acid sequence of a protein. They may occur in a region that does not code for a protein, or they may occur within a codon in a manner that does not alter the final amino acid sequence. However, a silent mutation in the exon/intron border may lead to alternative splicing by changing the splice site, thereby leading to a changed protein.

Mutations resulting in a non-functional gene avert the expression of the respective gene as a functional protein. Such mutations can be achieved by various approaches of gene technology known to those skilled in the art. Preferred herein is the disruption of those parts of the genes which encode those sites of enzymes which are necessary for enzyme activity. Most preferred is the deletion of the whole gene encoding the respective enzyme.

A polynucleotide can be isolated using standard molecular biology techniques and a known sequence information, e.g. as provided herein. Synthetic oligonucleotide primers for polymerase chain reaction amplification can be designed based upon a known nucleotide sequence. A nucleic acid molecule can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligo-nucleotides can be prepared by standard synthetic techniques, e.g., using an automated DNA synthesizer.

"Gene regulation" is the general control of gene expression. The general concept of gene regulation is the same in all types of cells, however with some specificities in prokaryots and eukaryots. The one skilled in the art is well aware about the differences, e.g. in bacteria, gene regulation is organized in operons. "Induction" is the process of triggering gene expression, whereas "repression" designates the inhibition of gene expression. A prominent example for the induction of gene expression in $E.$ $coli$ is the fact that IPTG is able to bind the lac-repressor (product of expression of the lad gene) and thereby triggering the expression of those (trans)genes which are regulated by the lac-repressor. Other prominent induction systems are e.g. heat induction or induction by quorum sensing. The one skilled in the art is familiar with such techniques.

An "operon" can be regulated positively or negatively. Positive regulation needs an activator for RNA polymerase which binds the DNA to start transcription. Negative regulation is triggered by a repressor gene, which codes for a regulatory protein that binds to the operator and inhibits transcription. Regulatory genes need not be part of the operon itself, but may be located elsewhere in the genome. Furthermore, certain substrates might drive gene regulation by binding activators or repressors.

A "vector" is a DNA molecule used as a vehicle to transfer foreign genetic material into a host cell. The four major types of vectors are "plasmids", "viral vectors", "cosmids", and "artificial chromosomes". Common components of vectors are an origin of replication, a multiple cloning site, and a selectable marker. The vector itself is generally a DNA sequence that consists of an insert (or transgene) and a larger sequence that serves as the "backbone" of the vector. The purpose of a vector which transfers genetic information to a host cell is typically to isolate, multiply, or express the insert (or transgene) in the host cell. Vectors called "expression vectors" (or expression constructs) specifically are designated for the expression of a transgene in a host cell, and generally have a promoter sequence that drives expression of the transgene in the host cell.

As used herein with respect to a recombinant expression vector, "operatively linked" is intended to mean that the nucleotide sequence of interest is linked to the regulatory sequence(s) in a manner which allows for expression of the nucleotide sequence. The term "regulatory sequence" is intended to include promoters, enhancers, and other expression control elements (e.g. polyadenylation signals). Such regulatory sequences are well known in the art. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc.

The recombinant expression vectors of the invention comprise nucleic acids as described herein in a form suitable for expression of the nucleic acids in a host cell, which means that the recombinant expression vectors include one or more regulatory sequences, selected on the basis of the host cells to be used and/or the desired circumstances for expression, which is operatively linked to the nucleic acid sequence to be expressed. The isolated recombinant expression vector of the invention preferably comprises a polynucleotide encoding a polypeptide in a host cell allowing the conversion of glycerol into serinol as compared to control cells of the same genetic background. More preferably, the expression of the said polynucleotide is controlled by induction.

The expression vectors of the invention can be introduced into host cells to thereby produce polypeptides encoded by nucleic acids as described herein. In general, insertion of a vector into a host cell is usually called transformation for bacterial cells, transfection for eukaryotic cells, although insertion of a viral vector is often called transduction. Herein, a polynucleotide may be "introduced" into a host cell by any means, including transfection, transformation or transduction, electroporation, particle bombardment, and the like. The introduced polynucleotide may be maintained in the cell stably if it is incorporated into a non-chromosomal autonomous replicon or integrated into the chromosomes. Alternatively, the introduced polynucleotide may be present on an extra-chromosomal non-replicating vector and may be transiently expressed or transiently active.

The use of natural promoters to trigger transgenic expression is also called "gene regulation" herein. To make use of natural promoters in terms of controlling the expression of a transgene, it is required to insert the transgene in the vicinity of the promoter. Such an insertion is realized e.g. by homologous recombination events. The one skilled in the art is familiar with such techniques. The transgene should be followed at least by a terminator if the gene which is naturally controlled by such a promoter should not be expressed any more in the host cells. Preferred herein is to use those promoters for regulation of the desired transgenes which normally control the expression of those genes encoding the enzymes which should be inactivated in their enzyme activity for the purpose of the invention.

Regarding the gene products of interest for the invention the following applies:

Polypeptides expressed in microorganisms can be detected by various techniques known to those skilled in the art. Therefore, the effects of genetic modification often can be assessed by analysis of the protein pattern expressed, e.g. by protein analysis techniques like proteomics.

Specifically, enzymatic activities (or the catalytic activity of enzymes) can be analyzed by using enzyme activity assays. The determination of activities and kinetic parameters of enzymes is well established in the art. Experiments to determine the activity of any given altered enzyme must be tailored to the specific activity of a non-altered enzyme, which is well within the ability of one skilled in the art. Overviews about enzymes in general, as well as specific details concerning structure, kinetics, principles, methods, applications and examples for the determination of many enzyme activities are abundant and well known to one skilled in the art.

On the one hand, enzymes might be "inactive for" their specificity or function, meaning the enzyme is present in an altered functional (reduced catalytic activity) or even non-functional form (lack of catalytic activity). Such an inactivation might be achieved either on DNA level by mutation of at least those codons of a gene encoding the respective enzyme which are responsible for its activity or specificity. An inactivation of an enzyme might also be achieved by substrates binding to the relevant parts of an enzyme to inhibit its function. Such substances are called enzyme inhibitors.

The enzyme activity assay would therefore be used to identify the residual catalytic activity of the enzyme which was targeted to be inactivated. Compared to fully active enzymes, inactivated enzymes show activities reduced at least by 50%, 60%, 70%, 80%, or 90% up to 100%. Specifically, this means, the residual catalytic activity is less than 50% to 0%, 40% to 0%, 30% to 0%, 20% to 0%, 10% to 0%, 5% or 0%.

On the other hand, enzymes not expressed in a wild-type strain, might have been introduced into a host cell strain by molecular biological techniques. To analyze, whether the transgene is expressed as a functional enzyme in the host cells, enzyme activity assays inform about the catalytic activity of the desired gene product. In this case the goal is to evaluate, whether the host cells harboring the desired transgene are "active for" the function of a specific enzyme in the sense of showing the desired catalytic activity.

In this context it should be noted, that "homologs" are defined herein as two nucleic acids or polypeptides that have similar, or substantially identical, nucleotide or amino acid sequences. Homologs include allelic variants, analogs, and orthologs. The term homolog further encompasses nucleic acid molecules that differ from one of the nucleotide of the invention due to degeneracy of the genetic code and thus encode the same polypeptide. Therefore, genes to be expressed might on the one hand be not identical but homolog to the sequences as displayed in the sequence listing of this invention but encode for a polypeptide or enzyme which equals the polypeptide sequence as displayed in the sequence listing of the current invention and therefore having the desired function or catalytic activity. On the other hand, the enzyme expressed might be not identical but homolog to the polypeptide sequences as displayed in the sequence listing of the current invention, however does show the desired function or catalytic activity. Herein it is preferred, that the homologues of a nucleic acid sequence encode for a polypeptides having the desired enzyme function or catalytic activity or homologues of polypeptide sequences which have the desired enzyme function or catalytic activity.

Herein, the expression of the gene product of the rtxA gene, i.e. dihydroxyacetone phosphate aminotransferase/dihydrorhizobitoxine synthase, is important to allow the conversion of glycerol to serinol in host cell cultures. The rtxA gene according to SEQ ID NO:1 encodes the dihydroxyacetone phosphate aminotransferase/dihydrorhizobitoxine synthase according to SEQ ID NO:2. However, it is the expression of a functional enzyme which is desired herein. Preferably, the transgene is a polynucleotide encoding the functional protein corresponding to amino acids 25-325 of SEQ ID NO:2 which is responsible for the transaminase activity. More preferably, the transgene is the N-terminal region of the rtxA gene, i.e. 346 N-terminal residues of SEQ ID NO:1, encoding a functional enzyme. The expression of a functional dihydroxyacetone phosphate aminotransferase, as it is called in short within this invention due to its desired function, can be determined by the dihydroxyacetone phosphate aminotransferase assay as described in Andreeβen B. and Steinbuechel A. (2012, Appl. Microbiol. Biotechnol. 93:357-365).

Another embodiment of the invention focuses on the expression of parts of the rtx operon together with the rtxA gene. Yasuta et al. 2001 (Appl. Environ. Microbiol. 67:4999-5009) designated the adjacent gene products as a putative glutamine amidotransferase according to SEQ ID NO:4 (encoded by rtxD gene according to SEQ ID NO:3), a putative transporter according to SEQ ID NO:6 (encoded by rtxE gene according to SEQ ID NO:5), a putative biotin carboxylase according to SEQ ID NO:8 (encoded by rtxF gene according to SEQ ID NO:7) and as a putative glutamine synthase according to SEQ ID NO:10 (encoded by rtxG gene according to SEQ ID NO:9). Preferred herein is the expression of the rtxA gene in combination with either rtxD, rtxE, rtxF, or rtxG. Other embodiments comprise the expression of the rtxA gene in every combination with other rtx genes, e.g. rtxEFG (meaning, that the rtx E, rtxF and rtxG are expressed in combination together with rtxA).

Other enzymes involved in the process of conversion of glycerol into serinol in microorganisms, are meant to be controlled in host cells in such a way, that the conversion of glycerol to serinol is established or increased compared to a control microorganism of the same genetic background. For this purpose it is preferred that enzymes negatively impacting the conversion of glycerol to serinol are inactivated in their enzyme specificity or catalytic activity.

Triosephosphate isomerase is the glycolytic enzyme that catalyzes the reversible interconversion of glyceraldehyde 3-phosphate (G3P) and dihydroxyacetone phosphate (DHAP). DHAP is an intermediate in the conversion of glycerol to serinol according to FIG. 2 and its supply should be maintained in terms of conversion of glycerol into serinol. A polynucleotide named tpiA (which is also called tpi often) as displayed in SEQ ID NO:11 encodes the triosephosphate isomerase with a polypeptide sequence as displayed in SEQ ID NO:12.

The goal is to inactivate the triosephosphate isomerase and thereby avert the isomerization of DHAP into G3P. Triosephosphate isomerase is known to be inhibited by several enzyme inhibitors known to those skilled in the art, e.g. 2-phospho glycolate. Preferably, the tpiA gene is disrupted such, that the enzyme activity of triosephosphate isomerase is inactivated in the sense of decreased. More preferred is the complete deletion of the tpiA gene as shown in SEQ ID NO:3 11 from the genome of the host cells. An activity assays for triosephosphate isomerase is described by Plaut B. and Knowles J. R. 1972 (The determination of triose phosphate isomerase, Biochem. J., 129:311-320).

Furthermore, DHAP can be metabolized by methylglyoxal synthase to methylglyoxal which may negatively impact (a) the serinol production itself in terms of lowering the DHAP level by metabolization of the needed DHAP and (b) the viability of the host cells by the production of methylglyoxal which is known to be toxic for cells. Methylglyoxal synthase with a sequence as displayed in SEQ ID NO:14 is encoded by the gene mgsA with a polynucleotide sequence as shown in SEQ ID NO:13.

The metabolization of DHAP to methylglyoxal should be averted herein. It is known that methylglyoxal synthase can be inhibited by several enzyme inhibitors known to those skilled in the art, e.g. 2-phospho glycolate. Preferably, the mgsA gene is disrupted such, that the enzyme activity of methylglyoxal synthase is inactivated in the sense of decreased. More preferred is the complete deletion of the mgsA gene as shown in SEQ ID NO:13 from the genome of the host cells. An activity assay for methylglyoxal phosphatase is described by Hopper D. J., and Cooper R. A. 1972 (Purification and properties of *Escherichia coli* methylglyoxal synthase, Biochem. J. 128:321-329).

The metabolization of glycerol into G3P is normally governed by the expression of members of the glp regulon: glycerol facilitator (encoded by glpF gene), glycerol kinase (encoded by glpK gene), G3P transport (encoded by glpT gene), anaerobic G3P dehydrogenase (encoded by glpA gene), aerobic G3P dehydrogenase (encoded by glpD gene), DNA-binding transcriptional repressor (encoded by glpR gene). The gene product of glpR represses the expression of the genes glpF, glpK and glpD (short glpFKD) or glpA (short glpFKA) in the absence of glycerol or G3P (Larson et al. 1987, Purification and characterization of the repressor for the sn-glycerol-3-phosphate regulon of Escherichia coli K-12, J. Biol. Chem. 262:15869-15874).

Herein, the metabolization of glycerol into G3P should be activated to improve the glycerol uptake and consequently the formation of DHAP. To inactivate the DNA-binding transcriptional repressor as displayed in SEQ ID NO:16 it would be necessary to use an inducer of gene expression in this case. Preferred herein is to target the glpR gene as displayed in SEQ ID NO:15 to be disrupted as such, as the expression of the DNA-binding transcriptional repressor is averted in its functional form. As a consequence activation of the expression of glpFKD or glpFKA should take place. An activity assay for glycerol kinase, which is an indirect proof for the repressor DNA-binding transcriptional repressor being inactive, is described by Freedberg W. B. and Lin E. C. C. 1973 (Three kinds of controls affecting the expression of the glp regulon in Escherichia coli, J. Bacteriol. 115(3):816-823).

Regarding the process to produce serinol

The invention comprises a process for producing serinol, which comprises the following steps:

i) culturing E. coli host cells inactive for triosephosphate isomerase and active for dihydroxyacetone phosphate aminotransferase to convert glycerol to serinol ii) induction of conversion from glycerol to serinol by at least adding glycerol to the cell culture ii) isolating serinol from the cell culture The E. coli host cells of the invention which are capable of converting glycerol to serinol by at least adding glycerol to the cell culture are described above. Under certain circumstances it is advisable to add further inducers which trigger the expression e.g. in the case of using an expression vector which is tailored specifically to be sensitive for induction. Prominent induction systems are e.g. chemical induction like the one with IPTG, heat induction or induction by quorum sensing. The one skilled in the art is familiar with such techniques.

Separating organic substances from mixtures, solutions and dispersions is a generally known task in the field of organic chemistry. Separation can be usually achieved by their physical and chemical properties such as boiling points, melting points, (non-)solubility in certain solvents, interaction between other chemical groups etc. Thus, depending on their chemical structure and their known or expected properties, a separation can be achieved by either crystallisation, distillation, rectification, all types of chromatography and membrane separations such as ultrafiltration and dialysis and all other separation and purification techniques known for organic substances. It is general knowledge of a person of skill in the art to evaluate the best suited method(s) and test and optimize the application of such methods for organic substances, especially when the chemical structure of these substances are known. Preferred herein is protonation of the amino-group of serinol and filtering the precipitate. Purification of the product is preferable done by chromatographic methods. For further details regarding serinol isolation and purification see for example U.S. Pat. No. 5,922,917A.

As used herein the term "room temperature" refers to a temperature between 20 and 25° C. It should be understood that this also means that the temperature is not critical for an experiment as long as it is carried out within the range of temperature given above. If in turn one experiment is carried out at 21° C. and another one at 23° C. both experiments are carried out within the definition "room temperature". In laboratory manuals and for numerical convenience 20° C. or 21° C. are often used.

EXAMPLES

Example 1

Media

B. elkanii USD94 (Yasuta et al. 2001) was cultivated at 25° C. in a modified arabinose gluconate medium (MAG, van Berkum 1990).

To produce serinol in batch cultures, cells were grown under aerobic conditions for 48 h to 72 h at 30° C. in Riesenberg (Rb) medium (Korz et al. 1987, Simple fed-batch technique for high cell density cultivation of Escherichia coli, J. Biotechnol. 39:59-65) containing 100 mM gluconate or glucose. After 12 h (gluconate) or 24 h (glucose), protein expression was induced and by adding 100 mM glycerol. All cultivations of E. coli were done under aerobic conditions at 37° C. in lysogeny broth (LB) medium (Sambrook et al. 1989, Molecular cloning: a laboratory manual, $2^{nd}$ edn. Cold Spring Harbor Laboratory, Cold Spring Harbor, N.Y.). Antibiotics were added in appropriate concentrations: ampicillin, 75 µg/ml; chloramphenicol, 25 µg/ml; gentamicin, 20 µg/ml; kanamycin, 50 µg/ml; rifampicin, 100 µg/ml; tetracyclin, 12.5 µg/ml. Further supplements were added like $NH^{4+}$ in the form of $(NH_4)_2HPO_4$ in concentrations of 40 mM, 100 mM, or 200 mM to optimize IPTG induction where desired.

Example 2

Isolation and Modification of DNA

All genetic techniques were performed as described by Sambrook et al. 1989 (Molecular cloning: a laboratory manual, $2^{nd}$ edn. Cold Spring Harbor Laboratory, Cold Spring Harbor, N.Y.). For amplification of rtxA, PCR was performed with an aliquot of genomic DNA of B. elkanii USD94-specific primers. The reaction was carried out in a PCR sprint thermocycler (Hybaid) using REDTaq® ReadyMix™ PCR Reaction Mix (Sigma-Aldrich Chemie, Steinheim, Germany). The corresponding fragments were separated in an agarose gel and were subsequently purified employing the peqGOLD Gel Extraction Kit (Peqlab Biotechnologie GmbH, Erlangen, Germany). For amplification of tpiA, mgsA, and glpR including their corresponding flanks chromosomal DNA of E. coli MG1655 and Phusion Polymerase (Finnzymes, Thermo Scientific, Vantaa, Finland) or REDTaq® ReadyMix™ PCR Reaction Mix (Sigma-Aldrich Chemie, Steinheim, Germany), respectively, has been used. The primers used for amplification were listed in table 1. All restriction enzymes were used from Fermentas, Thermo Scientific, St. Leon-Rot, Germany.

Example 3

Construction of the Deletion Cassettes

Deletion of triosephosphate isomerase. The PCR product (tpiA_sense/tpiA_anti) harbouring the tpiA gene and 300 bp of the upstream region and 400 bp of the downstream flank was ligated to the pJET vector (Fermentas, Thermo Scientific) according to the manufacturers guidelines. The fragment harbouring the rtxA gene under control of ptpiA1 was amplified with the primers rtxA_EcoRV_sense and rtxA_ptpiA1_anti and subcloned employing the TOPO TA Cloning® kit (Invitrogen, Life Technologies GmbH, Darmstadt, Germany). The plasmid pCR2.1 TOPO::ptpiA1::rtxA was digested with BamHI/Eco32I(EcoRV) and introduced in the BclI/Eco32I(EcoRV) digested vector pJET::tpiA yielding in pJETΔtpiA617-679(::ptpiA::rtxA). To get rid of the remaining part of tpiA, this construct was digested with AanI (PsiI) and religated [pJETΔtpiA(::ptpiA1::rtxA)]. For further selection of the deletion cassette the aacC1 gene enabling a gentamycin resistance was obtain from pSKsymΩGm (Overhage et al 1999, Biotransformation of eugenol to vanillin by a mutant of *Pseudomonas* sp. Strain HR199 constructed by disruption of the vanillin dehydrogenase (vdh) gene, Appl. Microbiol. Biotechnol. 52:820-828) by digestion with SmaI and introduced in the Eco32I(EcoRV) linearized pJETΔtpiA (::ptpiA::rtxA). Also a deletion of tpiA without insertion of rtxA was constructed. Therefore, the gentamycin resistance cassette from pSKsymΩGm was amplified using the primer pair SmaI_FRT_GmR_sense and SmaI_FRT_Gmr_anti, adding FRT sites for a later removal of the selection marker.

Deletion of methylglyoxal synthase. First, a fragment consisting of the mgsA gene 558 bp of the upstream and 578 bp of the downstream flank was amplified using the primer pair mgsA_sense/mgsA_anti and subcloned using the TOPO TA Cloning® kit (Invitrogen, Life Technologies GmbH, Darmstadt, Germany). To cut out the flanks and mgsA, the plasmid pCR 2.1 TOPO::mgsA was digested with BcuI(SpeI) and XhoI. This fragment was ligated to the pBBR1MCS-3 vector (BcuI(SpeI)/XhoI). For further selection of the deletion cassette the nptII gene enabling a kanamycin resistance was obtain from pSKsymΩKm (Overhage et al. 1999, Appl. Microbiol. Biotechnol. 52:820-828) by digestion with SmaI. The mgsA gene from plasmid pBBR1MCS-3::mgsA was replaced by the kanamycin resistance cassette using the restriction enzymes KspAI(HpaI) and SmaI.

Deletion of the glpR DNA-binding transcriptional repressor. The gene encoding for this repressor including a 892 bp upstream and a 929 bp downstream region was amplified with the primer glpR_sense and glpR_anti. The PCR product was subcloned utilizing the TOPO TA Cloning® kit (Invitrogen, Life Technologies GmbH, Darmstadt, Germany), digested with BamHI and XhoI and ligated to the pBBR1MCS-1 vector cut with the same enzymes. The glpR gene was exchanged by the FRT-GmR-FRT cassette by digestion of pBBR1MCS-1::glpR with AanI(PsiI)/PdmI(XmnI) and ligated with the SmaI cut selection marker.

For the chromosomal deletions the Red®/ET® Quick & Easy Gene Deletion Kit (Gene bridges, Heidelberg, Germany) has been used according to the manufacturers guidelines. Of course for the resistance cassettes the specifics needed were acknowledged. The one skilled in the art is aware of such adaptions in general protocols.

Example 4

Cloning of the rtx Operon

To elucidate the influence of the residual enzymes part of the rtxACDEFG operon, different combinations of were constructed. As vector backbone pCOLADuet-1 (Novagen, Merck KgaA, Darmstadt, Germany) has been chosen. The rtxA gene was amplified employing the primer rtxA_VspI_sense and rtxA_EcoRI_anti (Andreeβen and Steinbüchel 2012, Appl. Microbiol. Biotechnol. 93:357-365), digested with VspI(AseI) and EcoRI and ligated into the second multiple cloning site of pCOLADuet-1, (NdeI/MunI (MfeI). The gene encoding a putative glutamine amidotransferase (rtxD) was amplified with the primer pair rtxD_NcoI_sense/rtxD_BamHI_anti, for the isolation of the fragment harboring a putative transporter (rtxE), a putative biotin carboxylase (rtxF) and a putative glutamine synthase (rtxG) was the primer rtxE_BamHI_sense and rtxG_NotI_anti were used. The PCR products were digested with BamHI/NcoI and BamHI/NotI, respectively and ligated into the first multiple cloning site of pCOLADuet-1 or pCOLADuet-1::rtxD and cut with the corresponding enzymes. To gain the plasmids pCOLADuet-1::rtxD::rtxA, pCOLADuet-1::rtxEFG::rtxA and pCOLADuet-1::rtxDEFG::rtxA, pCOLADuet-1::rtxD, pCOLADuet-1::rtxEFG and pCOLADuet-1::rtxDEFG, respectively, were digested with (NotI/XbaI) and introduced to pCOLADuet-1::rtxA.

TABLE 2

Plasmids used and constructed

| Plasmid | Description | Reference/Source |
|---|---|---|
| pBBR1MCS-1 | Cm$^r$ | Kovach et al. (1995) |
| pBBR1MCS-1::glpR | Cm$^r$, glpR from *E. coli* MG1655 | herein |
| pBBR1MCS-3 | Tc$^r$ | Kovach et al. (1995) |
| pBBR1MCS-3::mgsA | Tc$^r$, mgsA from *E. coli* MG1655 | herein |
| pCOLADuet-1 | Km$^r$ | Novagen, Merck KgaA |
| pCOLADuet-1::rtxA | Km$^r$, rxtA from *B. elkanii* USD94 | herein |
| pCOLADuet-1::rtxD | Km$^r$, rxtD from *B. elkanii* USD94 | herein |
| pCOLADuet-1::rtxD::rtxA | Km$^r$, rxtAD from *B. elkanii* USD94 | herein |
| pCOLADuet-1::rtxDEFG::rtxA | Km$^r$, rxtADEFG from *B. elkanii* USD94 | herein |
| pCOLADuet-1::rtxEFG | Km$^r$, rxtEFG from *B. elkanii* USD94 | herein |
| pCOLADuet-1::rtxEFG::rtxA | Km$^r$, rxtAEFG from *B. elkanii* USD94 | herein |
| pCR 2.1 TOPO | Ap$^r$, Km$^r$ | Invitrogen |
| pCR 2.1 TOPO::glpR | Ap$^r$, Km$^r$, glpR from *E. coli* MG1655 | herein |
| pCR 2.1 TOPO::mgsA | Ap$^r$, Km$^r$, mgsA from *E. coli* MG1655 | herein |
| pCR2.1 TOPO::ptpiA1::rtxA | Ap$^r$, Km$^r$, ptpiA1 from *E. coli* MG1655, rtxA from *B. elkanii* USD94 | herein |
| pJET | Ap$^r$ | Fermentas, Thermo Scientific |
| pJET::tpiA | Ap$^r$, tpiA from *E. coli* MG1655 | herein |
| pJETΔtpiA(::ptpiA1::rtxA) | Ap$^r$, ptpiA1 from *E. coli* MG1655, rtxA from *B. elkanii* USD94 | herein |
| pJETΔtpiA617-679 | Ap$^r$, tpiA1-617 from *E. coli* MG1655, | herein |

TABLE 2-continued

Plasmids used and constructed

| Plasmid | Description | Reference/Source |
|---|---|---|
| (::ptpiA1::rtxA) | rtxA from *B. elkanii* USD94 | |
| pSKsymΩGm | Ap$^r$, Gm$^r$-cassette | Overhage et al. (1999) |
| pSKsymΩKm | Ap$^r$, Km$^r$-cassette | Overhage et al. (1999) |

TABLE 3

List of primers used. Restriction sites are underlined, start or stop codons are in bold letters, FRT recognition sites are italicized

| Name | Sequence | Tm [°C.] |
|---|---|---|
| glpR_anti | 5'-ACGCTTTATACTGTCCCCTTTTGTG-3' (SEQ ID NO: 17) | 61.3 |
| glpR_sense | 5'-GGCGCGGGCAAGTCATTTC-3' (SEQ ID NO: 18) | 61.0 |
| mgsA_anti | 5'-ACCGCTGGTGGTCAGTTTTAATACCC-3' (SEQ ID NO: 19) | 64.8 |
| mgsA_sense | 5'-TCAGCAGAACCCAGGCCAGCTG-3' (SEQ ID NO: 20) | 65.8 |
| rtxA_EcoRV_sense | 5'-AATCCGGCA<u>GATATC</u>AGACTCAGATTGCGGAAAGCGCCCTG-3' (SEQ ID NO: 21) | 71.4 |
| rtxA_ptpiA1_anti | 5'-<u>TTATAA</u>GCGTGGAGAATTAAAATGCTGCTCGACCTCGCATC-3' (SEQ ID NO: 22) | 74.1 |
| rtxD_BamHI_anti | 5'-CGTCACAA<u>GGATCC</u>TCTAATGTTTCTTTGTTTGG-3' (SEQ ID NO: 23) | 67.1 |
| rtxD_NcoI_sense | 5'-AAG<u>GGGCCC</u>ATGGCATGACATTGCAAC-3' (SEQ ID NO: 24) | 68.0 |
| rtxE_BamHI_sense | 5'-ATTAG<u>AGGATCC</u>TTATGACGTTTCAAACCAAGCG-3' (SEQ ID NO: 25) | 67.1 |
| rtxG_NotI_anti | 5'-AGCT<u>CGCGGCCGC</u>TAAATGATCTCGAAATAC-3' (SEQ ID NO: 26) | 69.5 |
| SmaI_FRT_GmR_anti | 5'-TTT<u>CCCGGG</u>*AAGTTCCTATACTTTCTAGAGAATAGGAACTTCAG*CCGATCTCGGCTTGAACGAATTGTTAG-3' (SEQ ID NO: 27) | — |
| SmaI_FRT_GmR_sense | 5'-AAA<u>CCCGGG</u>*GAAGTTCCTATTCTCTAGAAAGTATAGGAACTTC*GAGAGGCGGTTTGCGTATTGGGCGCATGC-3' (SEQ ID NO: 28) | — |
| tpiA_anti | 5'-ATTCAAATGACCTGGCTACCCATCC-3' (SEQ ID NO: 29) | 63.0 |
| tpiA_sense | 5'-TTTGCGCGGGCATGAATACCTG-3' (SEQ ID NO: 30) | 62.1 |

Example 5

Introduction of Deletion Cassettes and Vectors

The deletion cassettes for the tpiA gene, mgsA gene, and/or glpR gene where introduced into the *E. coli* host cells by electroporation. Transformation with the pCOLADuet-1 vectors of the invention was done by using chemical competent cells (CaCl$_2$ method of Hanahan et al. 1983, Studies on transformation of *Escherichia coli* with plasmids. J. Mol. Biol. 166:557-580).

Example 6

Serinol Detection

HPLC. The serinol content was determined by high-pressure liquid chromatography (HPLC) (Aboulmagd et al. 2000, Molecular characterization of the cyanophycin synthetase from *Synechocystis* sp. Strain PCC6308, Arch. Microbiol. 174:297-306) using a Waters B801 column (300 by 4 mm). Pre-column ortho-phthaldialdehyde (OPA) derivatization was performed using a Smartline autosampler 3900 as described in the manual (Knauer, Berlin, Germany). Calibration was done with commercially purchased serinol with a purity of 98% which was acknowledged within the calculations made herein (Sigma-Aldrich, Steinheim, Germany).

GC/MS. The serinol content was also determined by gas chromatography mass spectrometry (GC/MS) with a capillary gas chromatograph (Series 6890 GC System, Hewlett Packard, Waldbronn). Therefore 500 µl of the supernatant was freeze dried, resolved in 300 µl pyridine and 20 µl MSTFA (N-methyl-N-(trimethylsilyl)-trifluoracetamide) for derivatisation was added. The reaction mixture was incubated at 60° C. for 1 h. The samples were separated on a BPX35 capillary column (35% Diphenyl 65% Dimethyl Polysil Phenylene-siloxane; length: 60 m; inner diameter: 0.22 mm; film thickness: 250 nm; stationary phase: polyethylene glycol, Fa. SGE Deutschland GmbH, Darmstadt) with helium (99.999% Fa. Messer, Griesheim, Germany) as carrier gas at a flow rate of 0.6 ml min$^{-1}$. The organic phase (3 µl) was injected by an autosampler (Series 7683 Injector, Hewlett Packard, Waldbronn, Germany). The column admittance temperature was 60° C.; the column exit temperature was 290° C. For an efficient sample separation a multilevel temperature program was used: 2 min constant at 60° C., 5° C. min$^{-1}$ increase in temperature until 170° C., 12° C. min$^{-1}$ increase in temperature until 290° C., 10 min constant at 290° C. The analysis of the data was carried out with a NIST-Mass Spectral Search Program (Stein et al. 1998, Windows Software Version 1.6d).

Example 7

Isolation and Purification of Serinol

Serinol was isolated by conversion into the corresponding hydrochloride (Nardi and Villa 1999, Process for the preparation of 2-amino-1,3-propanediol, U.S. Pat. No. 5,922,917A). The supernatant was adjusted with HCl to nearly pH 1 and incubated for 2 h at 40° C. The water was evaporated at reduced pressure and the precipitate was treated with 0.5 vol acetone under vigorous stirring at room temperature. The precipitating serinol hydrochloride was filtered on a RC-membrane filter with a pore size of 0.2 µm (Sartorius Stedim Biotech, Göttingen, Germany) and dried. Further purification was achieved using a DOWEX® 50WX8-100 ion-exchange resin (Sigma-Aldrich Chemie, Steinheim, Germany). Elution was performed with 3 bed volumes of a 2M NH$_4$OH solution which was evaporated afterwards.

RESULTS

The most auspicious strain of the known art, i.e. *E. coli* HMS174(DE3)/pCDFDuet-1::rtxA in its context of the disclosure uses glycerol on the one hand as substrate (educt) for the serinol production. On the other hand, glycerol served as carbon source for the growth of the host cell culture. Notably, the growth behavior of *E. coli* HMS174(DE3) wild-type strain on different carbon sources (i.e. glycerol, gluconate, glucose) was the same, meaning that it is not decisive for this wild-type strain which carbon source was used when cultured (data not shown).

The consideration was made to specify the role of glycerol as being the substrate for the serinol production only. Consequently, the carbon source for cell growth of the host strain was decided to be changed.

In terms of being able to convert glycerol into serinol, it is necessary, that the rtxA gene is expressed in the host cells. In contrast to the known approach, in the current approach, the vector pCOLADuet-1 was used for transformation of the host cells with the transgene rtxA. The plasmid is called pCOLA-Duet-1::rtxA herein.

Having analyzed the growth properties of the *E. coli* HMS174(DE3)ΔtpiA/pCOLADuet-1::rtxA strain, it has been figured out that the cells grow well in the presence of glucose and/or gluconate. The overall growth of the cells was better in the presence of gluconate compared to the growth in the presence of glucose. In contrast, the cells showed only marginal growth in the presence of glycerol. Therefore, compared to the known strains of the art, the herein established *E. coli* HMS 174(DE3)ΔtpiA/pCOLADuet-1::rtxA strain is not able to use glycerol as carbon source any more.

Using the already furnished *E. coli* HMS 174(DE3)ΔtpiA strain, the mgsA gene was inactivated in the next step by deletion, establishing the mutated *E. coli* HMS174(DE3)ΔtpiAΔmgsA/pCOLADuet-1::rtxA strain. The analysis of the growth properties of this strain inactivated for tpiA and mgsA showed a comparable situation like for the *E. coli* HMS174 (DE3)ΔtpiA/pCOLADuet-1::rtxA strain. The same was true for the strain inactivated for tpiA, mgsA and glpR which is called *E. coli* HMS 174(DE3)ΔtpiAΔmgsAΔglpR/pCOLADuet-1::rtxA herein.

One of the conclusions of the disclosure from Andreeßen and Steinbüchel (2012, Appl. Microbiol. Biotechnol. 93:357-365) was that induction with IPTG (Isopropyl-β-D-thiogalactopyranoside; induction by binding a lac-repressor) leads to inclusion body formation and lowers serinol production in the *E. coli* HMS174(DE3) strain of the disclosure harboring the plasmids pACYCDuet-1::rtxA or pCDFDuet-1::rtxA. This phenomenon was already observed at rather low levels of 0.1 mM IPTG. Therefore, the IPTG inducible plasmid carrying *E. coli* strains appeared not to meet the goal to improve serinol production.

In contrast to the known approach, in the current approach, the vector pCOLADuet-1::rtxA was used for transformation of the host cells. Glycerol was added to the host cell culture for the purpose to be converted into serinol after 12 h in the case of gluconate being the carbon source or 24 h in the case of glucose being the carbon. IPTG was added for induction at the same time. In contrast to the already known strains of the art, IPTG induction worked successfully. Serinol concentration was increased by supplementation of the growth medium with 100 mM glycerol and 0.1 mM IPTG or 1 mM IPTG in the presence of 40 mM NH$_4$2HPO$_4$, 100 mM NH$_4$2HPO$_4$ or 200 mM NH$_4$2HPO$_4$. The best results were achieved when 1 mM IPTG were added into a medium containing 40 mM NH$_4$2HPO$_4$.

Surprisingly, the two mutant *E. coli* strains, HMS174(DE3)ΔtpiA/pCOLADuet-1::rtxA, and HMS174(DE3)ΔtpiAΔmgsA/pCOLADuet-1::rtxA produced approximately 3.3 g/l (100 mM glycerol and 1 mM IPTG were added after 12 h of culture on gluconate) and approximately 3.5 g/l (100 mM glycerol and 1 mM IPTG were added after 24 h of culture on glucose) serinol when cultured for 48 h. Specifically, for *E. coli* HMS174(DE3)ΔtpiAΔmgsA/pCOLADuet-1::rtxA the conversion rates were thereby increased up to 36.1% (gluconate) and 38.7% (glucose), respectively. For detailed data see Table 4.

The inactivation of the tpiA gene and the inactivation of the tpiA gene in combination with the inactivation of the mgsA gene lead to similar results in terms of rates of conversion from glycerol to serinol in the mutant *E. coli* HMS 174(DE3) strains harboring the pCOLADuet-1::rtxA plasmid after 48 h of culture on either gluconate or glucose. However, the ΔtpiAΔmgsA mutant was more productive compared to the ΔtpiA mutant when grown on glucose in an earlier stage of the culture, i.e. between 24 h to 36 h of culture.

The triple inactivated mutant *E. coli* HMS174(DE3)ΔtpiAΔmgsAΔglpR/pCOLADuet-1::rtxA appeared to be slightly less productive compared to the *E. coli* strains HMS174 (DE3)ΔtpiA/pCOLADuet-1::rtxA and HMS174(DE3)ΔtpiAΔmgsA/pCOLADuet-1::rtxA after 48 h of culture. On gluconate the serinol concentration achieved was 3.28 g/l (conversion rate: 30.2%), with glucose this yield was slightly higher (3.46 g/l, 31.8%). However, this *E. coli* HMS174 (DE3)ΔtpiAΔmgsAΔglpR/pCOLADuet-1::rtxA strain showed improved serinol production compared to the known strains from the art. For detailed data see Table 4.

The mutant strain *E. coli* HMS174(DE3)ΔtpiAΔmgsA/pCOLADuet-1::rtxDEFG::rtxA showed similar serinol productivity compared to *E. coli* HMS174(DE3)ΔtpiAΔmgsA/pCOLADuet-1::rtxA. The same was observed for *E. coli* HMS174(DE3)ΔtpiAΔmgsAΔglpR strains harboring pCOLADuet-1::rtxD::rtxA, pCOLADuet-1::rtxEFG::rtxA or pCOLADuet-1::rtxDEFG::rtxA, compared to E. coli HMS174(DE3)ΔtpiAΔmgsAΔglpR/pCOLADuet-1::rtxA strain. For detailed data see Table 4.

Further to the IPTG inducible strains of the invention, other E. coli strains became interesting for economic reasons of biotechnological serinol production. This holds true as the induction of gene expression with IPTG in a cell culture upscale raises costs of production substantially. Comparable considerations need to be made for any inducible system, meaning costs need to be weighed against benefit.

Therefore, to improve serinol production in systems different from the above described ones, an exchange of the tpiA gene with the rtxA gene was considered, to regulate the expression of rtxA by the natural tpiA promotors.

Following this reasoning, such a mutant was constructed in the background of E. coli MG1655 by chromosomal fusion of the rtxA gene with the natural tpiA-promotors ptpiA1 and ptpiA2.

Whereas the wild type strain E. coli MG1655 showed no differences in its growth behavior either on glucose, gluconate or glycerol (data not shown), the recombinant strain showed almost no growth on glycerol (see FIG. 3). The growth behavior on glucose as sole carbon source revealed to be comparable in the E. coli MG1655ΔtpiA(::rtxA) cells when compared to the E. coli HMS174(DE3)ΔtpiA/pCOLA-Duet-1::rtxA strain. The growth behavior on gluconate as sole carbon source however revealed to be increased in the E. coli MG1655ΔtpiA::rtxA cells compared to the E. coli HMS174(DE3)ΔtpiA/pCOLADuet-1::rtxA strain.

Regarding the production of serinol, similar observations were made in E. coli MG1655ΔtpiA(::rtxA) cells when compared to the E. coli HMS174(DE3)ΔtpiA/pCOLADuet-1::rtxA. The cultures of E. coli MG1655ΔtpiA(::rtxA) were supplemented with glycerol after 12 h leading to accumulation of up to 1.59 g/l (with gluconate as the carbon source) and 1.85 g/l (glucose) serinol with a conversion rate of 17.4% (w/w, gluconate) and 20.1% (w/w, glucose), respectively.

Further, following the reasoning from above, a double mutant E. coli MG1655ΔtpiA(::rtxA)ΔmgsA strain was established. Again the cells showed almost no growth on glycerol. The cell growth on glucose was decreased with respect to E. coli MG1655ΔtpiA(::rtxA). The growth behavior on gluconate however, was not influenced compared to E. coli MG1655ΔtpiA(::rtxA), and was again increased compared to the E. coli HMS174(DE3)ΔtpiAΔmgsA/pCOLA-Duet-1::rtxA strain.

The E. coli MG1655ΔtpiA(::rtxA)ΔmgsA strain produced 1.89 g/l (gluconate) and 2.32 g/l (glucose) serinol. The conversion rates of E. coli MG1655ΔtpiA(::rtxA)ΔmgsA were 20.6% (w/w, gluconate) and 25.2% (w/w, glucose). As the state of the art does not report about the actual amounts of glycerol used in the experiments, the conversion might be increased compared to the E. coli strains known in the prior art but need not necessarily be increased. However, the absolute amounts of serinol produced were in the range of the strains known from the prior art which were using the HMS 174(DE3) strain with the pCDFDuet-1::rtxA vector.

TABLE 4

Serinol production and conversion rates. All strains were grown in Riesenberg-medium (Korz et al. 1995, J Biotechnol. 39: 59-65). Induction and addition of 100 mM glycerol occurred after *12 h or **24 h. The E. coli HMS174(DE3) derived strains were induced by addition of 1 mM IPTG at the same time. The serinol content was determined by HPLC or GC/MS.

| E. coli strain | Sole carbon source | Induction | Serinol concentration [g/l] | Conversion rate [mg$_{serionl}$/g$_{glycerol}$] |
|---|---|---|---|---|
| MG1655ΔtpiA(::rtxA) | glucose | —* | 1.85 | 201 |
|  | gluconate | —* | 1.59 | 174 |
| MG1655ΔtpiA(::rtxA)ΔmgsA | glucose | —* | 2.32 | 252 |
|  | gluconate | —* | 1.89 | 206 |
| HMS174(DE3)/pCOLADuet-1::rtxA | glucose | 1 mM IPTG** | 2.56 | 278 |
|  | gluconate | 1 mM IPTG** | 2.42 | 263 |
| HMS174(DE3)ΔtpiA/pCOLADuet-1::rtxA | glucose | 1 mM IPTG** | 3.56 | 387 |
|  | gluconate | 1 mM IPTG* | 3.32 | 361 |
| HMS174(DE3)ΔtpiA/pCOLADuet-1::rtxD::rtxA | glucose | 1 mM IPTG** | 3.44 | 373 |
|  | gluconate | 1 mM IPTG* | 3.23 | 351 |
| HMS174(DE3)ΔtpiA/pCOLADuet-1::rtxEFG::rtxA | glucose | 1 mM IPTG** | 3.28 | 357 |
|  | gluconate | 1 mM IPTG* | 3.33 | 362 |
| HMS174(DE3)ΔtpiA/pCOLADuet-1::rtxDEFG::rtxA | glucose | 1 mM IPTG** | 3.47 | 377 |
|  | gluconate | 1 mM IPTG* | 3.30 | 359 |
| HMS174(DE3)ΔtpiAΔmgsA/pCOLADuet-1::rtxA | glucose | 1 mM IPTG** | 3.56 | 387 |
|  | gluconate | 1 mM IPTG* | 3.32 | 361 |
| HMS174(DE3)ΔtpiAΔmgsA/pCOLADuet-1::rtxDEFG::rtxA | glucose | 1 mM IPTG** | 3.54 | 385 |
|  | gluconate | 1 mM IPTG* | 3.34 | 365 |
| HMS174(DE3)ΔtpiAΔmgsAΔglpR/pCOLADuet-1::rtxA | glucose | 1 mM IPTG** | 3.46 | 318 |
|  | gluconate | 1 mM IPTG* | 3.28 | 302 |
| HMS174(DE3)ΔtpiAΔmgsAΔglpR/pCOLADuet-1::rtxDEFG::rtxA | glucose | 1 mM IPTG** | 3.27 | 327 |
|  | gluconate | 1 mM IPTG* | 3.30 | 303 |

The invention claimed is:

1. A recombinant *E. coli* strain active for dihydroxyacetone phosphate aminotransferase capable to convert glycerol to serinol, wherein triosephosphate isomerase is inactivated in the *E. coli* host cells.

2. The recombinant *E. coli* strain according to claim 1, wherein methylglyoxal synthase is inactivated additionally in the *E. coli* host cells.

3. The recombinant *E. coli* strain according to claim 1, wherein the glp DNA-binding transcriptional repressor is inactivated additionally in the *E. coli* host cells.

4. The recombinant *E. coli* strain according to claim 1, wherein active dihydroxyacetone phosphate aminotransferase is introduced into the said strain by transforming said strain with an expression vector comprising a transgene coding for dihydroxyacetone phosphate aminotransferase which is active for conversion of glycerol to serinol and wherein the expression of the dihydroxyacetone phosphate aminotransferase is inducible.

5. A recombinant *E. coli* strain selected from the group consisting of a. Strain *E. coli* MG1655ΔtpiA,
 b. Strain *E. coli* MG1655ΔtpiAΔmgsA,
 c. Strain *E. coli* MG1655ΔtpiAΔglpR, and
 d. Strain *E. coli* MG1655ΔtpiAΔmgsA ΔglpR, wherein said strain further comprises a gene encoding dihydroxyacetone phosphate aminotransferase(rtxA) and said rtxA is regulated by a natural promoter of tpiA and wherein said dihydroxyacetone phosphate aminotransferase is active for conversion of glycerol to serinol.

6. A recombinant *E. coli* strain selected from the group consisting of a. Strain *E. coli* HMS174(DE3)ΔtpiA,
 b. Strain *E. coli* HMS174(DE3)ΔtpiAΔmgsA,
 c. Strain *E. coli* HMS174(DE3)ΔtpiAΔglpR,
 d. Strain *E. coli* HMS174(DE3)ΔtpiAΔmgsAΔglpR, and wherein the strains are transformed with pCOLADuet-1::rtxA and wherein rtxA codes for dihydroxyacetone phosphate aminotransferase which is active for conversion of glycerol to serinol.

7. The recombinant *E. coli* strain according to claim 6 wherein the strains are transformed with pCOLADuet-1::rtxD::rtxA.

8. The recombinant *E. coli* strain according to claim 6 wherein the strains are transformed with pCOLADuet-1::rtxEFG::rtxA.

9. The recombinant *E. coli* strain according to claim 6 wherein the strains are transformed with pCOLADuet-1::rtxDEFG::rtxA.

10. A process for producing serinol, which comprises
   i) culturing *E. coli* host cells inactive for triosephosphate isomerase and active for dihydroxyacetone phosphate aminotransferase to convert glycerol to serinol,
   ii) induction of conversion from glycerol to serinol by adding at least glycerol to the cell culture, and
   iii) isolating serinol from the cell culture.

11. The process according to claim 10, wherein the *E. coli* host cells are in addition inactive for methylglyoxal synthase.

12. The process according to claim 10, wherein glp DNA-binding transcriptional repressor is inactivated additionally in the *E. coli* host cells.

13. The process according to claim 10, wherein expression of active dihydroxyacetone phosphate aminotransferase is achieved by introducing an expression vector into the host cells comprising the transgene coding for dihydroxyacetone phosphate aminotransferase which is active for conversion of glycerol to serinol.

\* \* \* \* \*

SEQUENCE LISTING

<160> NUMBER OF SEQ ID NOS: 30

<210> SEQ ID NO 1
<211> LENGTH: 2412
<212> TYPE: DNA
<213> ORGANISM: Bradyrhizobium elkanii

<400> SEQUENCE: 1

```
atgctgctcg acctcgcatc gcgcgatggt gagttcaagg aagtgaccgc ccgcatgagg     60
cggctgatgc tcaatctgct gggaggtgcc aaggactatt cggtggtccc cattcagggg    120
ggcgggtcct ttgcaatgga agccgcgctc tcttcattcg tgtccaggaa cgacaagccg    180
ctcgtttgca taaacggcat ctatggcgag cgcattttca agattctgcg gctgtggggc    240
gtcgaagcgc tgaagcttgt caagcgagcg accgagcccc tggagcccca ggaagttgcc    300
gagcagctga gccgaaatcc cggcgttact cacctatgtc ttgtgcattg cgagacaaca    360
accggaatcg tcaatccggt tgacgcgatc atagaggagg cgaggcggcg tggtgtgaag    420
acgatcgtcg acggcatgag ctcttttggc gcgattgaca tcgacctaag ccgtggtgga    480
ccggatgtcc tggtcacatc gagcaataag tgcatcgaag gccgccagg  agtagctttt    540
gtcatcgcgt ctcgcgagct gctggaaaaa gcggttcaag aaccaaggtc atttgtgctc    600
gacgtgagag accaatggct ctcgctcgag cgtaccggag agtggcgatc gaccccaccc    660
acccacatcg ttcaggcaac aacgaaggct ttggagattc tggaggggga gggcattgat    720
gccaggcgcc gcaggtatga aaggtcaga  gacgatctcg tccaagaact cgaagggta    780
gtgtctccgc tgctatccgc cgaattgcag tctccggtct gcgtcgcgtt cagggcgccg    840
tccggaatcg cggatcaggc aggcttcgat gggctatatc gtcacttggc ggcccacaat    900
ctttatatct actcgaagct gcatcttgcg acgcggagtt ttcgggtcgg ctgcattggc    960
gagatccagc ccagttggat cgagcagttg gggtgcgcct ttcgtacata ttttcggtcc   1020
ggcccggctt catccatggg gacgccgtca acccgccagg cctgcgagcg tggggtcgag   1080
atgtcatcgt ccttcgcaaa ggactcgcag ctgccgttct ctgccgaaac tgctgttctg   1140
cacgccggct accgacgcga tccggtgacg aaagctgtcg cagtgccgat ctatcagaac   1200
acggcttacg aacttgatgg cgatctgaat cacattgcgg acgtctataa cgtcaaggct   1260
gatggattca cctatacgag gatcatcaac ccgacgaccc gcgcgctgga aaaaaggtat   1320
gccgcggtcg acatgggaag cgactcgctc gccgtcgcat caggtcaagc ggcaaccttc   1380
cttgccatcg tcaacctgtc aagcggcgag gtggggaca  atatcgtcgc ctcaccgtat   1440
ctctatggca acacgtggaa tctgctccat aacacgctga gcgtcttgg  tatcagcgtc   1500
agaacggcag accccgaag  gcccgagacc ttcaacgtg  ccatcgatga tcgcacgatc   1560
tgcctgttcg agaggtgat  ttcaaatcct tgcctgattc cgcttccggt caaacagctg   1620
gctgagatcg gccgaaagca cggcgttccg ttggtggtgg ataatacgac gaccccgctg   1680
gtatgtcggc cgtcagatct cggtgctgcg attacgacct actccgctac gaaatacata   1740
tgcggccatg gcacaacgct gggcggtctg atcgttgaca acggcaagtt cagctaccgc   1800
ggcgcctctc gctttcccttg  ttcaacagt cctgacgagg cgcatggcgg gatcatctgg   1860
cgcaacgcgc tgcaagatgt cgacgatctc ggaaaaagcg aggttctctt gaaggctcgc   1920
atgacctggt tgcgcgatac tggcgcggcc attgccccct ttgcgagctt tcagctgatc   1980
caaggccttg aaacgctgcc ccttcgcatg aagcagcact gcgcaaacgc caggatcgtg   2040
gccgacgttc ttaaggagca tccaaaaagtg cgccgcgtct tctacccggg gctgttcgag   2100
ggagccgatc gggaaactgt cgaccagaca ctcaatcccg catacggaca cggcgcgatg   2160
gtcatgttcg aagttgagga cgagcaggcc gggcggaaat tcatccagaa tgtcgacctg   2220
atgtatcacg tctcgaatgt cggggacgcc cgtacgctcg taacgcatcc tgtttcgacc   2280
```

```
acccacacca ctgttccgcg ggagaagcgc gaagccgccg gcatatttgg cggctcgatc    2340
cgactttgcg tgggcatcga agatgtcgac gacatcgtgc gcgatctgga cagggcgctt    2400
tccgcaatct ga                                                        2412
```

<210> SEQ ID NO 2
<211> LENGTH: 803
<212> TYPE: PRT
<213> ORGANISM: Bradyrhizobium elkanii

<400> SEQUENCE: 2

```
Met Leu Leu Asp Leu Ala Ser Arg Asp Gly Glu Phe Lys Glu Val Thr
1               5                   10                  15

Ala Arg Met Arg Arg Leu Met Leu Asn Leu Leu Gly Gly Ala Lys Asp
            20                  25                  30

Tyr Ser Val Val Pro Ile Gln Gly Gly Ser Phe Ala Met Glu Ala
        35                  40                  45

Ala Leu Ser Ser Phe Val Ser Arg Asn Asp Lys Pro Leu Val Cys Ile
    50                  55                  60

Asn Gly Ile Tyr Gly Glu Arg Ile Phe Lys Ile Leu Arg Leu Trp Gly
65                  70                  75                  80

Val Glu Ala Leu Lys Leu Val Lys Arg Ala Thr Glu Pro Leu Glu Pro
                85                  90                  95

Gln Glu Val Ala Glu Gln Leu Ser Arg Asn Pro Gly Val Thr His Leu
            100                 105                 110

Cys Leu Val His Cys Glu Thr Thr Thr Gly Ile Val Asn Pro Val Asp
        115                 120                 125

Ala Ile Ile Glu Glu Ala Arg Arg Arg Gly Val Lys Thr Ile Val Asp
    130                 135                 140

Gly Met Ser Ser Phe Gly Ala Ile Asp Ile Asp Leu Ser Arg Gly Gly
145                 150                 155                 160

Pro Asp Val Leu Val Thr Ser Ser Asn Lys Cys Ile Glu Gly Pro Pro
                165                 170                 175

Gly Val Ala Phe Val Ile Ala Ser Arg Glu Leu Leu Glu Lys Ala Val
            180                 185                 190

Gln Glu Pro Arg Ser Phe Val Leu Asp Val Arg Asp Gln Trp Leu Ser
        195                 200                 205

Leu Glu Arg Thr Gly Glu Trp Arg Ser Thr Pro Pro Thr His Ile Val
    210                 215                 220

Gln Ala Thr Thr Lys Ala Leu Glu Ile Leu Glu Gly Glu Gly Ile Asp
225                 230                 235                 240

Ala Arg Arg Arg Arg Tyr Glu Lys Val Arg Asp Asp Leu Val Gln Glu
                245                 250                 255

Leu Glu Gly Val Val Ser Pro Leu Leu Ser Ala Glu Leu Gln Ser Pro
            260                 265                 270

Val Cys Val Ala Phe Arg Ala Pro Ser Gly Ile Ala Asp Gln Ala Gly
        275                 280                 285

Phe Asp Gly Leu Tyr Arg His Leu Ala Ala His Asn Leu Tyr Ile Tyr
    290                 295                 300

Ser Lys Leu His Leu Ala Thr Arg Ser Phe Arg Val Gly Cys Ile Gly
305                 310                 315                 320

Glu Ile Gln Pro Ser Trp Ile Glu Gln Leu Gly Cys Ala Phe Arg Thr
                325                 330                 335

Tyr Phe Arg Ser Gly Pro Ala Ser Ser Met Gly Thr Pro Ser Thr Arg
            340                 345                 350
```

```
Gln Ala Cys Glu Arg Gly Val Glu Met Ser Ser Phe Ala Lys Asp
        355                 360                 365
Ser Gln Leu Pro Phe Ser Ala Glu Thr Ala Val Leu His Ala Gly Tyr
    370                 375                 380
Arg Arg Asp Pro Val Thr Lys Ala Val Ala Val Pro Ile Tyr Gln Asn
385                 390                 395                 400
Thr Ala Tyr Glu Leu Asp Gly Asp Leu Asn His Ile Ala Asp Val Tyr
            405                 410                 415
Asn Val Lys Ala Asp Gly Phe Thr Tyr Thr Arg Ile Ile Asn Pro Thr
                420                 425                 430
Thr Arg Ala Leu Glu Lys Arg Tyr Ala Ala Val Asp Met Gly Ser Asp
        435                 440                 445
Ser Leu Ala Val Ala Ser Gly Gln Ala Ala Thr Phe Leu Ala Ile Val
    450                 455                 460
Asn Leu Ser Ser Gly Glu Val Gly Asp Asn Ile Val Ala Ser Pro Tyr
465                 470                 475                 480
Leu Tyr Gly Asn Thr Trp Asn Leu Leu His Asn Thr Leu Lys Arg Leu
            485                 490                 495
Gly Ile Ser Val Arg Thr Ala Asp Pro Arg Pro Glu Thr Phe Glu
                500                 505                 510
Arg Ala Ile Asp Asp Arg Thr Ile Cys Leu Phe Gly Glu Val Ile Ser
        515                 520                 525
Asn Pro Cys Leu Ile Pro Leu Pro Val Lys Gln Leu Ala Glu Ile Gly
    530                 535                 540
Arg Lys His Gly Val Pro Leu Val Val Asp Asn Thr Thr Thr Pro Leu
545                 550                 555                 560
Val Cys Arg Pro Ser Asp Leu Gly Ala Ala Ile Thr Thr Tyr Ser Ala
            565                 570                 575
Thr Lys Tyr Ile Cys Gly His Gly Thr Thr Leu Gly Gly Leu Ile Val
                580                 585                 590
Asp Asn Gly Lys Phe Ser Tyr Arg Gly Ala Ser Arg Phe Pro Leu Phe
        595                 600                 605
Asn Ser Pro Asp Glu Ala His Gly Gly Ile Ile Trp Arg Asn Ala Leu
    610                 615                 620
Gln Asp Val Asp Asp Leu Gly Lys Ser Glu Val Leu Leu Lys Ala Arg
625                 630                 635                 640
Met Thr Trp Leu Arg Asp Thr Gly Ala Ala Ile Ala Pro Phe Ala Ser
            645                 650                 655
Phe Gln Leu Ile Gln Gly Leu Glu Thr Leu Pro Leu Arg Met Lys Gln
                660                 665                 670
His Cys Ala Asn Ala Arg Ile Val Ala Asp Val Leu Lys Glu His Pro
        675                 680                 685
Lys Val Arg Arg Val Phe Tyr Pro Gly Leu Phe Glu Gly Ala Asp Arg
    690                 695                 700
Glu Thr Val Asp Gln Thr Leu Asn Pro Ala Tyr Gly His Gly Ala Met
705                 710                 715                 720
Val Met Phe Glu Val Glu Asp Glu Gln Ala Gly Arg Lys Phe Ile Gln
            725                 730                 735
Asn Val Asp Leu Met Tyr His Val Ser Asn Val Gly Asp Ala Arg Thr
                740                 745                 750
Leu Val Thr His Pro Val Ser Thr Thr His Thr Thr Val Pro Arg Glu
        755                 760                 765
```

-continued

```
Lys Arg Glu Ala Ala Gly Ile Phe Gly Gly Ser Ile Arg Leu Cys Val
    770                 775                 780

Gly Ile Glu Asp Val Asp Asp Ile Val Arg Asp Leu Asp Arg Ala Leu
785                 790                 795                 800

Ser Ala Ile

<210> SEQ ID NO 3
<211> LENGTH: 819
<212> TYPE: DNA
<213> ORGANISM: Bradyrhizobium elkanii

<400> SEQUENCE: 3
atgacattgc aacgctcaga caacgctcgc gccgtggtcg gcgtcacctc gaaccgtctt      60
ttggtcgatg gtgtgcatcg cgactggcta cggcaaaaat acctcaaggc cctccttcat     120
catgcgggcg tggcatgcgt catattgccg acgatcgacg cggaagatgt gaggctagag     180
gtcggcctgg cgatcatggg cgcgctcgac ggtctggttt tgacagggga tgaatcgaat     240
attgaccctg ccgtcttgaa ggcacctgca tcacttccgc cggctgacca acaggacgtt     300
gatggtggaa ttcgtgaccg cccgcgggat aggctctctg cggtagccat tgggagcgcc     360
atcgcgctcg gaatgccgat cttgggcatc tgccgcgggc ttcaggagct caacgtctat     420
tttggcggca ctctccatcc atcgcttgct gagtggagac tgggaagtgg cctgatgcat     480
gccgagaaac cagatcgtcc aagagaccgt cagtacgatg ccgcgcacag cgtgaggata     540
tctcctgatg gtgcgctctt tccgatcgtg cgcgccatcg aagcgcaagt gaactccctg     600
cataatcaag gcatcgagct gcttgccgcc gcactgaggc gcgaggcatg ggcgcctgac     660
ggactggtcg aagcggcttc ggtcatcggc gcgccgacgt tgcaaatcgg tgtgcaatgg     720
caccccgaat ggcacgcctc aactgatctc ctgagccagc gactgttcac ggcttttgga     780
gaggcgtgtg ttgcgtacta ccaaacaaag aaacattag                            819

<210> SEQ ID NO 4
<211> LENGTH: 272
<212> TYPE: PRT
<213> ORGANISM: Bradyrhizobium elkanii

<400> SEQUENCE: 4

Met Thr Leu Gln Arg Ser Asp Asn Ala Arg Ala Val Val Gly Val Thr
1               5                   10                  15

Ser Asn Arg Leu Leu Val Asp Gly Val His Arg Asp Trp Leu Arg Gln
            20                  25                  30

Lys Tyr Leu Lys Ala Leu Leu His His Ala Gly Val Ala Cys Val Ile
        35                  40                  45

Leu Pro Thr Ile Asp Ala Glu Asp Val Arg Leu Glu Val Gly Leu Ala
    50                  55                  60

Ile Met Gly Ala Leu Asp Gly Leu Val Leu Thr Gly Asp Glu Ser Asn
65                  70                  75                  80

Ile Asp Pro Ala Val Leu Lys Ala Pro Ala Ser Leu Pro Pro Ala Asp
                85                  90                  95

Gln Gln Asp Val Asp Gly Gly Ile Arg Asp Arg Pro Arg Asp Arg Leu
            100                 105                 110

Ser Ala Val Ala Ile Gly Ser Ala Ile Ala Leu Gly Met Pro Ile Leu
        115                 120                 125

Gly Ile Cys Arg Gly Leu Gln Glu Leu Asn Val Tyr Phe Gly Gly Thr
    130                 135                 140
```

Leu His Pro Ser Leu Ala Glu Trp Arg Leu Gly Ser Gly Leu Met His
145                 150                 155                 160

Ala Glu Lys Pro Asp Arg Pro Arg Asp Arg Gln Tyr Asp Ala Ala His
            165                 170                 175

Ser Val Arg Ile Ser Pro Asp Gly Ala Leu Phe Pro Ile Val Arg Ala
            180                 185                 190

Ile Glu Ala Gln Val Asn Ser Leu His Asn Gln Gly Ile Glu Leu Leu
        195                 200                 205

Ala Ala Ala Leu Arg Arg Glu Ala Trp Ala Pro Asp Gly Leu Val Glu
    210                 215                 220

Ala Ala Ser Val Ile Gly Ala Pro Thr Leu Gln Ile Gly Val Gln Trp
225                 230                 235                 240

His Pro Glu Trp His Ala Ser Thr Asp Leu Leu Ser Gln Arg Leu Phe
            245                 250                 255

Thr Ala Phe Gly Glu Ala Cys Val Ala Tyr Tyr Gln Thr Lys Lys His
            260                 265                 270

<210> SEQ ID NO 5
<211> LENGTH: 1023
<212> TYPE: DNA
<213> ORGANISM: Bradyrhizobium elkanii

<400> SEQUENCE: 5
atgacgtttc aaaccaagcg cggtccgccc aggtcgaaag gtgagtcttc cggaactggt      60
ggacaagcgt ggtccggggg gcgggccgcg ccgccccgcc gcagaggac gggtgggcga      120 ttgacaagac gcttcgctct gggagttctc tttgtagcgc tctatgtcgt cctgagcgcg      180
gcaggcgaag tttatgcggc atcgtatttt cagcgggcgg atgcgttcgt cgctctcctc      240
gtgtcctttg ccgcggtctg tctgacattt aatctgctgg caggtcacga gagagaaacg      300 gcacggttg cgaagtcggc gctcctggtg ttcgtgtcgc tcaatgtcgt gaccgcgatc      360
agttggatcg ggttgtttat cggcctgaaa tacaccgaac cggcgatcgt cgtcgcgttc      420
atggtggcgc taggacccgc tgcgacggtg tggttaaacg cgctgatcag cgccagggc      480 gttcctccag catccgatat cgtcgtgagc gtgacgatcg cggcagttgg aagttacatg      540
atatggatct cggcaaccgg caacgctggc gtggagtggg gagctcgatc gtccttcggc      600
atcgtcttgg caatcgtggc cggcctatcg ctcgctctta caaatatact cgtcaagctg      660
ctattcgacc gcggattttc gggtcgacag gtgttggcgc atcgttttta cggaacgatc      720
cttttgctgc tgggactggt cgaccattcc tccatcgtgc tcgagatctc gcaacattgg      780
cttgcgatcg caacgattgg gctatccacg atcatcgttc cattgctctt gttccaggag      840
ggtattcgcc gcgtcgagcc cttcacggtc aacatggtcc tgtccaccgc tcctgtcatc      900
acgtttctgt tccagtactt cgattctcgt atcgtgcctt cgccgcatac gttcgttgga      960
aatgttctca tcacggctgt tgccgtcggc aacgtctgtt tgcagtaccg gaggtccgca     1020
tga                                                                    1023

<210> SEQ ID NO 6
<211> LENGTH: 340
<212> TYPE: PRT
<213> ORGANISM: Bradyrhizobium elkanii

<400> SEQUENCE: 6

Met Thr Phe Gln Thr Lys Arg Gly Pro Pro Arg Ser Lys Gly Glu Ser
1               5                   10                  15

```
Ser Gly Thr Gly Gly Gln Ala Trp Ser Gly Arg Ala Ala Pro Pro
            20                  25                  30

Arg Pro Gln Arg Thr Gly Arg Leu Thr Arg Phe Ala Leu Gly
        35                  40                  45

Val Leu Phe Val Ala Leu Tyr Val Leu Ser Ala Ala Gly Glu Val
 50                  55                  60

Tyr Ala Ala Ser Tyr Phe Gln Arg Ala Asp Ala Phe Val Ala Leu Leu
 65              70                  75                  80

Val Ser Phe Ala Ala Val Cys Leu Thr Phe Asn Leu Leu Ala Gly His
                85                  90                  95

Glu Arg Glu Thr Ala Arg Val Ala Lys Ser Ala Leu Leu Val Phe Val
                100                 105                 110

Ser Leu Asn Val Val Thr Ala Ile Ser Trp Ile Gly Leu Phe Ile Gly
            115                 120                 125

Leu Lys Tyr Thr Glu Pro Ala Ile Val Val Ala Phe Met Val Ala Leu
 130                 135                 140

Gly Pro Ala Ala Thr Val Trp Leu Asn Ala Leu Ile Arg Arg Gln Gly
145                 150                 155                 160

Val Pro Pro Ala Ser Asp Ile Val Val Ser Val Thr Ile Ala Ala Val
                165                 170                 175

Gly Ser Tyr Met Ile Trp Ile Ser Ala Thr Gly Asn Ala Gly Val Glu
            180                 185                 190

Trp Gly Ala Arg Ser Ser Phe Gly Ile Val Leu Ala Ile Val Ala Gly
        195                 200                 205

Leu Ser Leu Ala Leu Thr Asn Ile Leu Val Lys Leu Leu Phe Asp Arg
210                 215                 220

Gly Phe Ser Gly Arg Gln Val Leu Ala His Arg Phe Tyr Gly Thr Ile
225                 230                 235                 240

Leu Leu Leu Leu Gly Leu Val Asp His Ser Ser Ile Val Leu Glu Ile
                245                 250                 255

Ser Gln His Trp Leu Ala Ile Ala Thr Ile Gly Leu Ser Thr Ile Ile
            260                 265                 270

Val Pro Leu Leu Leu Phe Gln Glu Gly Ile Arg Arg Val Glu Pro Phe
        275                 280                 285

Thr Val Asn Met Val Leu Ser Thr Ala Pro Val Ile Thr Phe Leu Phe
 290                 295                 300

Gln Tyr Phe Asp Ser Arg Ile Val Pro Ser Pro His Thr Phe Val Gly
305                 310                 315                 320

Asn Val Leu Ile Thr Ala Val Ala Val Gly Asn Val Cys Leu Gln Tyr
                325                 330                 335

Arg Arg Ser Ala
            340
```

<210> SEQ ID NO 7
<211> LENGTH: 1290
<212> TYPE: DNA
<213> ORGANISM: Bradyrhizobium elkanii

<400> SEQUENCE: 7
atgaacgagc gaaactgtgt aatcgtcgac gcatattcga ccggccgctt cttgccggaa      60
gagttcaagc ggtatggaat ttcaacagtg catgtgatgt cggctgcaca gattccgtcg     120
atctttcaat cgcatttcaa tgctaatctg tatgatgaag tcattcgccc gcccgagcgc     180
atggggtacg acgagatcgt tgaatatcat cttcgggctc tccagggcag ggagctggag     240

```
ttcgtcatag cggggtgcga gacaggagtt gagctggccg attcgatctc ggagcggctg    300
ggcttgcctt caaatggcac cgcccttccg gccgcccgac gggacaaatc gcgcctgtct    360
gaagcgttgg cctcagcagg cgtgcgatcg atcagacaag tggtgtccga caatgctgaa    420
gtgatcgcaa gatggaagcg tcaagagacc ttcgatgagc ttgtgatcaa gccgctgaac    480
agcacaggca cggaggacgt gttcttttgc tcgacggatg ccgatattca gcgcgctgta    540
accgcgatcg tcggtaagac gaaccgtgtc ggaacgctca atcaattggc gcttggacag    600
gagaaaatca acggccagca atataccgta aatgccgtct cgatcgacgg cgagaccttc    660
gtcacggagg cctggaccta tgacactgtt cctattgagg cgcgtcttc ggtctgctca    720 ctcgagcggt tattgggagg taaggagcca atcgttcttg aactatccga ctaccttgaa    780
cgtgcgctgc gggcgcttcg gatcaccgac ggacctgctc atgccgagat catcgtcgat    840
gatcggggac cggttctggt cgacttcgga gcgaggctgc aaggaaccat gtcggcaaaa    900
gccaggacga tggcgttggg ccataaccat ttgacgctca ccgcgtggcg ttacgcagat    960
cccaaaggct ttgctgggta tatgaggcga cgcggggttt acaagcggca ggctcatgca   1020
ctgtgcgtct cgctgatctc cgacatgggc ggtgttgttg ccggctatcc cggactcgat   1080
gcgatcggca agctgccgag cttcgcggat gccattgcgt tcgttccgat agggcaaaac   1140
ctggttccga cgatcgactt ggcgtcgacg ccaggcattg tgtatctcgt gaacaacgac   1200
ctgatacagc ttgaggaaga ttatcgccaa ctgcgtgcga tgcggatgga ccaggtgttc   1260
gatttggtgc cgcaggaagc gaaccaatga                                    1290
```

<210> SEQ ID NO 8
<211> LENGTH: 429
<212> TYPE: PRT
<213> ORGANISM: Bradyrhizobium elkanii

<400> SEQUENCE: 8

```
Met Asn Glu Arg Asn Cys Val Ile Val Asp Ala Tyr Ser Thr Gly Arg
1               5                   10                  15

Phe Leu Pro Glu Glu Phe Lys Arg Tyr Gly Ile Ser Thr Val His Val
                20                  25                  30

Met Ser Ala Ala Gln Ile Pro Ser Ile Phe Gln Ser His Phe Asn Ala
            35                  40                  45

Asn Leu Tyr Asp Glu Val Ile Arg Pro Pro Glu Arg Met Gly Tyr Asp
        50                  55                  60

Glu Ile Val Glu Tyr His Leu Arg Ala Leu Gln Gly Arg Glu Leu Glu
65                  70                  75                  80

Phe Val Ile Ala Gly Cys Glu Thr Gly Val Glu Leu Ala Asp Ser Ile
                85                  90                  95

Ser Glu Arg Leu Gly Leu Pro Ser Asn Gly Thr Ala Leu Ser Ala Ala
            100                 105                 110

Arg Arg Asp Lys Ser Arg Leu Ser Glu Ala Leu Ala Ser Ala Gly Val
        115                 120                 125

Arg Ser Ile Arg Gln Val Val Ser Asp Asn Ala Glu Val Ile Ala Arg
    130                 135                 140

Trp Lys Arg Gln Glu Thr Phe Asp Glu Leu Val Ile Lys Pro Leu Asn
145                 150                 155                 160

Ser Thr Gly Thr Glu Asp Val Phe Phe Cys Ser Thr Asp Ala Asp Ile
                165                 170                 175

Gln Arg Ala Val Thr Ala Ile Val Gly Lys Thr Asn Arg Val Gly Thr
            180                 185                 190
```

Leu Asn Gln Leu Ala Leu Gly Gln Glu Lys Ile Asn Gly Gln Gln Tyr
        195                 200                 205

Thr Val Asn Ala Val Ser Ile Asp Gly Glu Thr Phe Val Thr Glu Ala
    210                 215                 220

Trp Thr Tyr Asp Thr Val Pro Ile Glu Gly Ala Ser Ser Val Cys Ser
225                 230                 235                 240

Leu Glu Arg Leu Leu Gly Gly Lys Glu Pro Ile Val Leu Glu Leu Ser
                245                 250                 255

Asp Tyr Leu Glu Arg Ala Leu Arg Ala Leu Arg Ile Thr Asp Gly Pro
            260                 265                 270

Ala His Ala Glu Ile Ile Val Asp Asp Arg Gly Pro Val Leu Val Asp
        275                 280                 285

Phe Gly Ala Arg Leu Gln Gly Thr Met Ser Ala Lys Ala Arg Thr Met
    290                 295                 300

Ala Leu Gly His Asn His Leu Thr Leu Thr Ala Trp Arg Tyr Ala Asp
305                 310                 315                 320

Pro Lys Gly Phe Ala Gly Tyr Met Arg Arg Gly Val Tyr Lys Arg
                325                 330                 335

Gln Ala His Ala Leu Cys Val Ser Leu Ile Ser Asp Met Gly Gly Val
            340                 345                 350

Val Ala Gly Tyr Pro Gly Leu Asp Ala Ile Gly Lys Leu Pro Ser Phe
        355                 360                 365

Ala Asp Ala Ile Ala Phe Val Pro Ile Gly Gln Asn Leu Val Pro Thr
    370                 375                 380

Ile Asp Leu Ala Ser Thr Pro Gly Ile Val Tyr Leu Val Asn Asn Asp
385                 390                 395                 400

Leu Ile Gln Leu Glu Glu Asp Tyr Arg Gln Leu Arg Ala Met Arg Met
                405                 410                 415

Asp Gln Val Phe Asp Leu Val Pro Gln Glu Ala Asn Gln
            420                 425

<210> SEQ ID NO 9
<211> LENGTH: 1335
<212> TYPE: DNA
<213> ORGANISM: Bradyrhizobium elkanii

<400> SEQUENCE: 9
atgaccggca tctgcgacag ttgcacgaat tcagccgctg cggcgatgat cggtgtgagc      60
gacttcgatg gcatccttcg aggcaaacac gtcctgggtg aagatctttc cgtcgggaat     120
aaggtcatca gttctctga agcggtgctc gcgtgggatt gttcggaccg cgtcattccg     180
gcgggcttca cgcaagagcc gcagtcagta tttggggacg ccgatctgcg cgttctgtcc     240
ggcaccggcc gttcggtgtc ttatgccggc gatcaatatc tctatctggc tgagtttgcg     300
ggcgcacatg agagcgtctg cccgcgcggt attctgcgta agtcctgca aagggttgcc     360 gaccgcggat acagctgcag cgccgggttc gagtttgagt ttatgctgtt caaggagaac     420
gccgacataa ttgaagacaa gccgttcggc caatgggctc ctttgacgcg gggcccattc     480
ggctactcga ttgcgcggtc tgtcgcgcac agggagctgt cggtgagat cctggcgctt     540 tgtgagaagt ccagaatccc tctcagcggg ctgcactttg aaacgggacc aggcgtgatc     600
gaagcgtcac ttcgtcattg tgatgccctg gaagccgccg atcgagcaat catattcaag     660
tcgatgataa aggcctgggc gcagacgcgc ggcatgatgg ctacattcat ggccaaggtt     720
tcagagaatt ggccgggcca gtccggccat attcacgtct cgatgtccgc agatggtcag     780

```
aatgtgtttt acgatagtga ggcgtttcgc aacgtctcga agctcatgag gcaattcatc    840
ggcggacaat tgaaatacat gaatgatttc tgtgtgctcg ctgtgccgaa tttcaatagc    900
tacaagagat tggtacctgg ttgttgggca ccaatctatc cgagctgggg aatcgacaac    960
cgatcctgcg cggtacgcgt cattccggga gacccgtctg cacatcgtct cgaatacagg   1020
ctgcccggtg cagacctgaa cccatatctt gccctcgcat gtgccatcgg ttccggcata   1080
ttgggtatcg agacaaacgc ggcgctcccg gcttcgatcg tcgtgatgc aagcgcggag    1140 gcctgccttc cgtctgggag gctgcctcaa agcttggcag aggcaacata tcggtttgca   1200
cagtctccgg cagccaatga tgtcttcggt gaaaggtttg ttgaagcgtt ttcttgctcc   1260
cgccgttggg aatgggaggc cgttcaacat cgggtcacag actttgaacg ccggcggtat   1320
ttcgagatca tttag                                                    1335
```

<210> SEQ ID NO 10
<211> LENGTH: 444
<212> TYPE: PRT
<213> ORGANISM: Bradyrhizobium elkanii

<400> SEQUENCE: 10

```
Met Thr Gly Ile Cys Asp Ser Cys Thr Asn Ser Ala Ala Ala Ala Met
1               5                   10                  15

Ile Gly Val Ser Asp Phe Asp Gly Ile Leu Arg Gly Lys His Val Leu
            20                  25                  30

Gly Glu Asp Leu Ser Val Gly Asn Lys Val Ile Lys Phe Ser Glu Ala
        35                  40                  45

Val Leu Ala Trp Asp Cys Ser Asp Arg Val Ile Pro Ala Gly Phe Thr
    50                  55                  60

Gln Glu Pro Gln Ser Val Phe Gly Asp Ala Asp Leu Arg Val Leu Ser
65                  70                  75                  80

Gly Thr Gly Arg Ser Val Ser Tyr Ala Gly Asp Gln Tyr Leu Tyr Leu
                85                  90                  95

Ala Glu Phe Ala Gly Ala His Glu Ser Val Cys Pro Arg Gly Ile Leu
            100                 105                 110

Arg Lys Val Leu Gln Arg Val Ala Asp Arg Gly Tyr Ser Cys Ser Ala
        115                 120                 125

Gly Phe Glu Phe Glu Phe Met Leu Phe Lys Glu Asn Ala Asp Ile Ile
    130                 135                 140

Glu Asp Lys Pro Phe Gly Gln Trp Ala Pro Leu Thr Arg Gly Pro Phe
145                 150                 155                 160

Gly Tyr Ser Ile Ala Arg Ser Val Ala His Arg Glu Leu Phe Gly Glu
                165                 170                 175

Ile Leu Ala Leu Cys Glu Lys Ser Arg Ile Pro Leu Ser Gly Leu His
            180                 185                 190

Phe Glu Thr Gly Pro Gly Val Ile Glu Ala Ser Leu Arg His Cys Asp
        195                 200                 205

Ala Leu Glu Ala Ala Asp Arg Ala Ile Ile Phe Lys Ser Met Ile Lys
    210                 215                 220

Ala Trp Ala Gln Thr Arg Gly Met Met Ala Thr Phe Met Ala Lys Val
225                 230                 235                 240

Ser Glu Asn Trp Pro Gly Gln Ser Gly His Ile His Val Ser Met Ser
                245                 250                 255

Ala Asp Gly Gln Asn Val Phe Tyr Asp Ser Glu Ala Phe Arg Asn Val
            260                 265                 270
```

```
Ser Lys Leu Met Arg Gln Phe Ile Gly Gly Gln Leu Lys Tyr Met Asn
        275                 280                 285

Asp Phe Cys Val Leu Ala Val Pro Asn Phe Asn Ser Tyr Lys Arg Leu
    290                 295                 300

Val Pro Gly Cys Trp Ala Pro Ile Tyr Pro Ser Trp Gly Ile Asp Asn
305                 310                 315                 320

Arg Ser Cys Ala Val Arg Val Ile Pro Gly Asp Pro Ser Ala His Arg
                325                 330                 335

Leu Glu Tyr Arg Leu Pro Gly Ala Asp Leu Asn Pro Tyr Leu Ala Leu
            340                 345                 350

Ala Cys Ala Ile Gly Ser Gly Ile Leu Gly Ile Glu Thr Asn Ala Ala
        355                 360                 365

Leu Pro Ala Ser Ile Val Gly Asp Ala Ser Ala Glu Ala Cys Leu Pro
    370                 375                 380

Ser Gly Arg Leu Pro Gln Ser Leu Ala Glu Ala Thr Tyr Arg Phe Ala
385                 390                 395                 400

Gln Ser Pro Ala Ala Asn Asp Val Phe Gly Glu Arg Phe Val Glu Ala
                405                 410                 415

Phe Ser Cys Ser Arg Arg Trp Glu Trp Glu Ala Val Gln His Arg Val
            420                 425                 430

Thr Asp Phe Glu Arg Arg Tyr Phe Glu Ile Ile
        435                 440
```

<210> SEQ ID NO 11
<211> LENGTH: 768
<212> TYPE: DNA
<213> ORGANISM: Escherichia coli

<400> SEQUENCE: 11

```
ttaagcctgt ttagccgctt ctgcagcttt aacgattact gcgaaggcgt cagctttcag    60
agaagcacca ccaaccagcg cgccgtcgat atccggctga gcaaacagtt ctgcagcgtt   120
agacgcgttt acagagccgc cgtactgaat gatcacttgt tcagcgatgt agcgtcaac    180
tttagcgatg tggtcacgga tgaatttgtg aacagcctgt gcctgagccg agttgcaga    240
tttgccagta ccgattgccc atacaggttc gtaagcgata ccgcacctt cgaatgccgc    300
agcaccctga gttttcagta ccgcgtcgat ctgacgtgcg caaacttctt cagttttgcc   360
cgcttcattt tcagcttcgg tttcaccgat gcacagaacc ggagtcaggc cctgctcttt   420
cagcaccgcg aatttttcg cgatcagttc gtcagattct tgtggtaag tacgacgttc    480
agagtgaccg atgatgatgt actgtgcgcc gatgtctttc agcatagcag cagaggtttc   540
accggtgaat cgccggaca ggttcaggtc cacgttttgc gcacccagca tgatgtggct    600
gccttcagct tcgcgcttcg ccatatcgat atacatttcc ggtggtgcga ttgcaaccgc    660
acagccagca cacctgcca gctctttacg caggttagaa accagctcgt gaaccatgtg    720
gcggctgccg ttcagtttcc agttacccat cactaaagga tgtcgcat              768
```

<210> SEQ ID NO 12
<211> LENGTH: 255
<212> TYPE: PRT
<213> ORGANISM: Escherichia coli

<400> SEQUENCE: 12

```
Met Arg His Pro Leu Val Met Gly Asn Trp Lys Leu Asn Gly Ser Arg
1               5                   10                  15
```

His Met Val His Glu Leu Val Ser Asn Leu Arg Lys Glu Leu Ala Gly
              20                  25                  30

Val Ala Gly Cys Ala Val Ala Ile Ala Pro Glu Met Tyr Ile Asp
          35                  40                  45

Met Ala Lys Arg Glu Ala Glu Gly Ser His Ile Met Leu Gly Ala Gln
 50                  55                  60

Asn Val Asp Leu Asn Leu Ser Gly Ala Phe Thr Gly Glu Thr Ser Ala
 65                  70                  75                  80

Ala Met Leu Lys Asp Ile Gly Ala Gln Tyr Ile Ile Gly His Ser
              85                  90                  95

Glu Arg Arg Thr Tyr His Lys Glu Ser Asp Glu Leu Ile Ala Lys Lys
             100                 105                 110

Phe Ala Val Leu Lys Glu Gln Gly Leu Thr Pro Val Leu Cys Ile Gly
             115                 120                 125

Glu Thr Glu Ala Glu Asn Glu Ala Gly Lys Thr Glu Glu Val Cys Ala
        130                 135                 140

Arg Gln Ile Asp Ala Val Leu Lys Thr Gln Gly Ala Ala Ala Phe Glu
145                 150                 155                 160

Gly Ala Val Ile Ala Tyr Glu Pro Val Trp Ala Ile Gly Thr Gly Lys
                165                 170                 175

Ser Ala Thr Pro Ala Gln Ala Gln Ala Val His Lys Phe Ile Arg Asp
            180                 185                 190

His Ile Ala Lys Val Asp Ala Asn Ile Ala Glu Gln Val Ile Ile Gln
        195                 200                 205

Tyr Gly Gly Ser Val Asn Ala Ser Asn Ala Ala Glu Leu Phe Ala Gln
210                 215                 220

Pro Asp Ile Asp Gly Ala Leu Val Gly Gly Ala Ser Leu Lys Ala Asp
225                 230                 235                 240

Ala Phe Ala Val Ile Val Lys Ala Glu Ala Ala Lys Gln Ala
                245                 250                 255

<210> SEQ ID NO 13
<211> LENGTH: 459
<212> TYPE: DNA
<213> ORGANISM: Escherichia coli

<400> SEQUENCE: 13
atggaactga cgactcgcac tttacctgcg cggaaacata ttgcgctggt ggcacacgat        60
cactgcaaac aaatgctgat gagctgggtg gaacggcatc aaccgttact ggaacaacac      120
gtactgtatg caacaggcac taccggtaac ttaatttccc gcgcgaccgg catgaacgtc      180
aacgcgatgt tgagtggccc aatgggggt gaccagcagg ttggcgcatt gatctcagaa       240
gggaaaattg atgtattgat tttcttctgg gatccactaa atgccgtgcc gcacgatcct      300
gacgtgaaag ccttgctgcg tctggcgacg gtatggaaca ttccggtcgc caccaacgtg      360
gcaacggcag acttcataat ccagtcgccg catttcaacg acgcggtcga tattctgatc      420
cccgattatc agcgttatct cgcggaccgt ctgaagtaa                              459

<210> SEQ ID NO 14
<211> LENGTH: 152
<212> TYPE: PRT
<213> ORGANISM: Escherichia coli

<400> SEQUENCE: 14

Met Glu Leu Thr Thr Arg Thr Leu Pro Ala Arg Lys His Ile Ala Leu
  1               5                  10                  15

```
Val Ala His Asp His Cys Lys Gln Met Leu Met Ser Trp Val Glu Arg
         20                  25                  30

His Gln Pro Leu Leu Glu Gln His Val Leu Tyr Ala Thr Gly Thr Thr
             35                  40                  45

Gly Asn Leu Ile Ser Arg Ala Thr Gly Met Asn Val Asn Ala Met Leu
 50                  55                  60

Ser Gly Pro Met Gly Gly Asp Gln Gln Val Gly Ala Leu Ile Ser Glu
 65                  70                  75                  80

Gly Lys Ile Asp Val Leu Ile Phe Phe Trp Asp Pro Leu Asn Ala Val
                 85                  90                  95

Pro His Asp Pro Asp Val Lys Ala Leu Leu Arg Leu Ala Thr Val Trp
            100                 105                 110

Asn Ile Pro Val Ala Thr Asn Val Ala Thr Ala Asp Phe Ile Ile Gln
            115                 120                 125

Ser Pro His Phe Asn Asp Ala Val Asp Ile Leu Ile Pro Asp Tyr Gln
        130                 135                 140

Arg Tyr Leu Ala Asp Arg Leu Lys
145                 150
```

<210> SEQ ID NO 15
<211> LENGTH: 759
<212> TYPE: DNA
<213> ORGANISM: Escherichia coli

<400> SEQUENCE: 15

```
atgaaacaaa cacaacgtca caacggtatt atcgaactgg ttaaacagca gggttatgtc    60
agtaccgaag agctggtaga gcatttctcc gtcagcccgc agactattcg ccgcgacctc   120
aatgagctgg cggagcaaaa cctgatcctg cgccatcatg cggtgcggc  gctgccttcc   180
agttcggtta acacgccgtg gcacgatcgc aaggccaccc agaccgaaga aaaagagcgc   240
atcgcccgca aagtggcgga gcaaatcccc aatggctcga cgctgtttat cgatatcggc   300
accacgccgg aagcggtagc gcacgcactg ctcaatcaca gcaatttgcg cattgtcacc   360
aacaatctca cgttgctaa  cacgttgatg gtaaaagaag attttcgcat cattctcgcc   420
ggtggcgaat tacgcagccg cgatggcggg atcattggcg aagcgacgct cgatttatc   480
tcccagttcc gccttgattt cggcattctg gggataagcg gcatcgatag cgacggctcg   540
ctgctggagt tcgattacca cgaagttcgc accaaacgcg ccattattga gaactcgcgc   600
cacgttatgc tggttgtcga tcactcgaaa tttggccgta acgcgatggt caatatgggc   660
agcatcagca tggtagatgc cgtctacacc gacgccccgc cgccagtaag cgtgatgcag   720
gtgctgacgg accaccatat tcaactggag ctgtgctga                          759
```

<210> SEQ ID NO 16
<211> LENGTH: 252
<212> TYPE: PRT
<213> ORGANISM: Escherichia coli

<400> SEQUENCE: 16

```
Met Lys Gln Thr Gln Arg His Asn Gly Ile Ile Glu Leu Val Lys Gln
 1               5                  10                  15

Gln Gly Tyr Val Ser Thr Glu Glu Leu Val Glu His Phe Ser Val Ser
                 20                  25                  30

Pro Gln Thr Ile Arg Arg Asp Leu Asn Glu Leu Ala Glu Gln Asn Leu
             35                  40                  45
```

```
Ile Leu Arg His His Gly Gly Ala Ala Leu Pro Ser Ser Val Asn
 50                  55                  60

Thr Pro Trp His Asp Arg Lys Ala Thr Gln Thr Glu Glu Lys Glu Arg
 65                  70                  75                  80

Ile Ala Arg Lys Val Ala Glu Gln Ile Pro Asn Gly Ser Thr Leu Phe
                 85                  90                  95

Ile Asp Ile Gly Thr Thr Pro Glu Ala Val Ala His Ala Leu Leu Asn
            100                 105                 110

His Ser Asn Leu Arg Ile Val Thr Asn Asn Leu Asn Val Ala Asn Thr
        115                 120                 125

Leu Met Val Lys Glu Asp Phe Arg Ile Ile Leu Ala Gly Gly Glu Leu
130                 135                 140

Arg Ser Arg Asp Gly Gly Ile Ile Gly Glu Ala Thr Leu Asp Phe Ile
145                 150                 155                 160

Ser Gln Phe Arg Leu Asp Phe Gly Ile Leu Gly Ile Ser Gly Ile Asp
                165                 170                 175

Ser Asp Gly Ser Leu Leu Glu Phe Asp Tyr His Glu Val Arg Thr Lys
            180                 185                 190

Arg Ala Ile Ile Glu Asn Ser Arg His Val Met Leu Val Val Asp His
        195                 200                 205

Ser Lys Phe Gly Arg Asn Ala Met Val Asn Met Gly Ser Ile Ser Met
210                 215                 220

Val Asp Ala Val Tyr Thr Asp Thr Met Pro Pro Ala Ser Val Met Gln
225                 230                 235                 240

Val Leu Lys Asp His His Ile Gln Leu Glu Leu Cys
                245                 250

<210> SEQ ID NO 17
<211> LENGTH: 25
<212> TYPE: DNA
<213> ORGANISM: Artificial Sequence
<220> FEATURE:
<223> OTHER INFORMATION: primer glpR_anti

<400> SEQUENCE: 17
acgctttata ctgtccccctt ttgtg                                       25

<210> SEQ ID NO 18
<211> LENGTH: 19
<212> TYPE: DNA
<213> ORGANISM: Artificial Sequence
<220> FEATURE:
<223> OTHER INFORMATION: primer glpR_sense

<400> SEQUENCE: 18
ggcgcgggca agtcatttc                                               19

<210> SEQ ID NO 19
<211> LENGTH: 26
<212> TYPE: DNA
<213> ORGANISM: Artificial Sequence
<220> FEATURE:
<223> OTHER INFORMATION: primer mgsA_anti

<400> SEQUENCE: 19
accgctggtg gtcagtttta ataccc                                       26

<210> SEQ ID NO 20
<211> LENGTH: 22
<212> TYPE: DNA
```

```
<213> ORGANISM: Artificial Sequence
<220> FEATURE:
<223> OTHER INFORMATION: primer mgsA_sense

<400> SEQUENCE: 20
tcagcagaac ccaggccagc tg                                              22

<210> SEQ ID NO 21
<211> LENGTH: 41
<212> TYPE: DNA
<213> ORGANISM: Artificial Sequence
<220> FEATURE:
<223> OTHER INFORMATION: primer rtxA_EcoRV_sense

<400> SEQUENCE: 21
aatccggcag atatcagact cagattgcgg aaagcgccct g                         41

<210> SEQ ID NO 22
<211> LENGTH: 41
<212> TYPE: DNA
<213> ORGANISM: Artificial Sequence
<220> FEATURE:
<223> OTHER INFORMATION: primer rtxA_ptpiA1_anti

<400> SEQUENCE: 22
ttataagcgt ggagaattaa aatgctgctc gacctcgcat c                         41

<210> SEQ ID NO 23
<211> LENGTH: 34
<212> TYPE: DNA
<213> ORGANISM: Artificial Sequence
<220> FEATURE:
<223> OTHER INFORMATION: primer rtxD_BamHI_anti

<400> SEQUENCE: 23
cgtcacaagg atcctctaat gtttctttgt ttgg                                 34

<210> SEQ ID NO 24
<211> LENGTH: 27
<212> TYPE: DNA
<213> ORGANISM: Artificial Sequence
<220> FEATURE:
<223> OTHER INFORMATION: primer rtxD_NcoI_sense

<400> SEQUENCE: 24
aaggggccca tggcatgaca ttgcaac                                         27

<210> SEQ ID NO 25
<211> LENGTH: 34
<212> TYPE: DNA
<213> ORGANISM: Artificial Sequence
<220> FEATURE:
<223> OTHER INFORMATION: primer rtxE_BamHI_sense

<400> SEQUENCE: 25
attagaggat ccttatgacg tttcaaacca agcg                                 34

<210> SEQ ID NO 26
<211> LENGTH: 31
<212> TYPE: DNA
<213> ORGANISM: Artificial Sequence
<220> FEATURE:
<223> OTHER INFORMATION: primer rtxG_NotI_anti

<400> SEQUENCE: 26
agctcgcggc cgctaaatga tctcgaaata c                                    31
```

```
<210> SEQ ID NO 27
<211> LENGTH: 71
<212> TYPE: DNA
<213> ORGANISM: Artificial Sequence
<220> FEATURE:
<223> OTHER INFORMATION: primer SmaI_FRT_GmR_anti

<400> SEQUENCE: 27
tttcccggga agttcctata ctttctagag aataggaact tcagccgatc tcggcttgaa        60
cgaattgtta g                                                            71

<210> SEQ ID NO 28
<211> LENGTH: 72
<212> TYPE: DNA
<213> ORGANISM: Artificial Sequence
<220> FEATURE:
<223> OTHER INFORMATION: primer SmaI_FRT_GmR_sense

<400> SEQUENCE: 28
aaacccgggg aagttcctat tctctagaaa gtataggaac ttcgagaggc ggtttgcgta        60
ttgggcgcat gc                                                           72

<210> SEQ ID NO 29
<211> LENGTH: 25
<212> TYPE: DNA
<213> ORGANISM: Artificial Sequence
<220> FEATURE:
<223> OTHER INFORMATION: primer tpiA_anti

<400> SEQUENCE: 29
attcaaatga cctggctacc catcc                                             25

<210> SEQ ID NO 30
<211> LENGTH: 22
<212> TYPE: DNA
<213> ORGANISM: Artificial Sequence
<220> FEATURE:
<223> OTHER INFORMATION: primer tpiA_sense

<400> SEQUENCE: 30
tttgcgcggg catgaatacc tg                                                22
```